(12) United States Patent
Kuusela et al.

(10) Patent No.: US 11,651,848 B2
(45) Date of Patent: May 16, 2023

(54) METHODS AND APPARATUS FOR CONTROLLING TREATMENT DELIVERY USING REINFORCEMENT LEARNING

(71) Applicant: Siemens Healthineers International AG, Steinhausen (CH)

(72) Inventors: Esa Heikki Kuusela, Espoo (FI); Shahab Basiri, Espoo (FI); Elena Czeizler, Helsinki (FI); Mikko Oskari Hakala, Rajamäki (FI); Lauri Jaakonpoika Halko, Helsinki (FI)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 490 days.

(21) Appl. No.: 16/832,115

(22) Filed: Mar. 27, 2020

(65) Prior Publication Data

US 2021/0304866 A1 Sep. 30, 2021

(51) Int. Cl.
*A61N 5/10* (2006.01)
*G16H 20/40* (2018.01)
*G16H 50/20* (2018.01)
*G16H 30/40* (2018.01)

(52) U.S. Cl.
CPC .......... *G16H 20/40* (2018.01); *A61N 5/1038* (2013.01); *A61N 5/1039* (2013.01); *A61N 5/1067* (2013.01); *A61N 5/1071* (2013.01); *G16H 30/40* (2018.01); *G16H 50/20* (2018.01); *A61N 2005/1072* (2013.01); *A61N 2005/1074* (2013.01)

(58) Field of Classification Search
CPC ...... A61N 5/10–1084; A61N 2005/1085–1098
See application file for complete search history.

(56) References Cited

U.S. PATENT DOCUMENTS

| 2008/0039713 | A1* | 2/2008 | Thomson | A61N 5/1039 382/294 |
| 2019/0333623 | A1 | 10/2019 | Hibbard | |
| 2020/0129780 | A1* | 4/2020 | Lachaine | A61N 5/1037 |
| 2020/0360728 | A1* | 11/2020 | Tilly | A61B 5/7267 |
| 2021/0027878 | A1* | 1/2021 | He | G16H 50/70 |

FOREIGN PATENT DOCUMENTS

WO 2007012185 A1 2/2007

* cited by examiner

*Primary Examiner* — Thaddeus B Cox
(74) *Attorney, Agent, or Firm* — Potomac Law Group, PLLC

(57) ABSTRACT

Methods and systems are provided which relate to the planning and delivery of radiation treatments by modalities which involve moving a radiation source along a trajectory relative to a subject while delivering radiation to the subject. An artificial intelligence (AI) agent trained using reinforcement learning (and/or some other suitable form of machine learning) is used to control the radiation delivery parameters in effort to achieve desired delivery of radiation therapy. In some embodiments, the AI agent selects suitable control steps (e.g. radiation delivery parameters for particular time steps), while accounting for patient motions, difference(s) in patient anatomical geometry and/or the like.

19 Claims, 7 Drawing Sheets

METHODS AND APPARATUS FOR CONTROLLING TREATMENT DELIVERY USING REINFORCEMENT LEARNING

TECHNICAL FIELD

This invention relates to radiation treatment. The invention relates particularly to methods and apparatus employing an artificial intelligence agent, configured (trained) using machine learning, to control a radiation delivery apparatus and to thereby provide a three-dimensional distribution of radiation dose.

BACKGROUND

The delivery of carefully-planned doses of radiation may be used to treat various medical conditions. For example, radiation treatments are used, often in conjunction with other treatments, in the treatment and control of cancers. While it can be beneficial to deliver appropriate amounts of radiation to certain structures or tissues, in general, radiation can harm living tissue. It may therefore be desirable to target radiation on a target volume containing the structures or tissues to be irradiated while minimizing (or keeping to a clinically acceptable level) the dose of radiation delivered to surrounding tissues. Intensity modulated radiation therapy (IMRT) is one method that has been used to deliver radiation to target volumes in living subjects while mitigating the amount of radiation absorbed by surrounding tissues.

IMRT typically involves delivering shaped radiation beams from a few different directions. For each direction, a cross-section of the beam may be shaped to conform to the projection of the target volume in the beam's-eye-view (i.e. a view taken along a central axis of the radiation beam, abbreviated as BEV). Beams may additionally or alternatively have other cross-sectional shapes. The radiation beams are typically delivered in sequence. The radiation beams each contribute to the desired dose in the target volume.

A typical radiation delivery apparatus has a source of radiation, such as a linear accelerator, and a rotatable gantry. The gantry can be rotated to cause a radiation beam to be incident on a subject from various different angles. The shape of the incident radiation beam can be modified by a multi-leaf collimator (MLC). An MLC has a number of leaves which are mostly opaque to radiation. The MLC leaves define an aperture through which radiation can propagate. The positions of the leaves can be adjusted to change the shape of the aperture and to thereby shape the radiation beam that propagates through the MLC. The MLC may also be rotatable (e.g. about the BEV axis) to different angles.

Methods disclosed in the prior art for delivering doses of radiation involve first planning the dose distribution to be delivered. Such planning may involve selecting a sequence of control points at which a radiation dose is delivered and, for each control point, a corresponding set of radiation delivery parameters. The locations of control points and the parameters of the radiation delivery apparatus may be assigned within the solution space of all candidate solutions (e.g. optimized) to determine the dose that is delivered at each control point and to determine the trajectory of the corresponding radiation beam. Some of these prior art methods comprise selecting control points and/or radiation delivery parameters which optimize the geometric radiation distribution between planning target volumes and organ-at-risk (OAR) volumes to minimize radiation exposure to critical structures while ensuring sufficient radiation delivered to target tissue. A dose distribution is typically planned using previously gathered patient images, to evaluate that the plan achieves the clinically desired treatment.

Typically, treating a patient comprises administering a plurality of temporally spaced apart treatment fractions (or, for brevity, fractions). During each treatment fraction, the radiation delivery apparatus is typically operated automatically over the course of the treatment fraction based on the selected (e.g. planned) sequence of control points and corresponding radiation delivery parameters. At each control point, radiation is delivered to the subject using a set of parameters (for the radiation delivery apparatus) which are predefined during the planning process (e.g. optimized) according to clinical goals. The control point may specify locations along a trajectory at which the radiation source should be positioned and the radiation delivery apparatus parameters may define the characteristics of the beam at each control point. The only interactive action in these types of prior art treatment fractions is usually the early termination of the planned delivery sequence in the case of unexpected events, such as the subject changing positions abruptly. Motions due to breathing cycles or intestinal gas induced motion within a treatment fraction (e.g. within a normal amplitude range) may be considered typical patient motions. Such typical patient motions are generally considered (in the prior art) to be within "expected limits" and do not lead to the termination or modification of the treatment fraction. However, since treatment plans are typically created and optimized based on stationary planning images, any spatial deviation (e.g. typical patient motions) results in sub-optimal dose distribution. There is no guarantee that this sub-optimality is small.

As between radiation delivery fractions or as between imaging and the delivery of any fraction, a patient's anatomical geometry (e.g. the corresponding geometry between target tissue and healthy tissue) may change. For example, a patient may lose weight, organs may shift relative to one within a patient's abdominal cavity, the geometry of target tissue may change and/or the like.

There have been various attempts in the prior art to address changes in patient geometry which may occur during any particular treatment fraction, between treatment fractions and/or between imaging and any treatment fraction. Such strategies include tracking, which attempts to move the patient (e.g. by moving the couch on which the patient is located) or the beam aperture to attempt to follow a target aperture; gating which involves completely turning off the radiation source in response to breathing cycle monitoring; and adaptive treatment which permits inter-fraction treatment adjustments. These prior art attempts have mitigated the issues associated with patient geometry movement to some degree, the each have their disadvantages.

Despite the advances that have been made in the field of radiation therapy, there remains a general desire for radiation treatment methods and apparatus and radiation treatment planning methods and apparatus that provide improved control over the delivery of radiation, for example, by delivering suitable dose to target tissues and keeping dose delivered to healthy tissues to a clinically acceptable level. There is a general desire that such improved control accommodate factors such as patient movement, differences in the geometry of patient anatomy and/or the like.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

Aspects of the invention relate to the planning and delivery of radiation treatments by modalities which involve moving a radiation source along a trajectory relative to a subject while delivering radiation to the subject. An artificial intelligence (AI) agent trained using reinforcement learning (and/or some other suitable form of machine learning) is used to control the radiation delivery parameters in effort to achieve desired delivery of radiation therapy. In some embodiments, the AI agent selects suitable control steps (e.g. radiation delivery parameters for particular time steps), while accounting for patient motions, difference(s) in patient anatomical geometry and/or the like.

One non-limiting aspect of the invention provides a method for determining radiation dose to deliver to a patient using a radiation delivery apparatus. The method comprises: providing a radiation delivery apparatus comprising a radiation source and one or more moveable elements; defining a machine state, the machine state comprising positions of the one or more moveable elements and wherein, when the radiation source is active, the machine state defines characteristics of radiation emitted by the radiation delivery apparatus; for each of a plurality of time steps in a radiation delivery fraction: receiving, at an artificial intelligence (AI) agent comprising a processor configured to execute software instructions: a set of observations regarding the machine state and regarding geometry of the patient; determining, by the AI agent, a current treatment state of the patient based at least in part on the set of observations; determining, by the AI agent, a next action comprising a next machine state for a subsequent time step based at least in part on the current treatment state and an artificial intelligence (AI) policy determined a priori using a machine-learning process executed on training data, the next machine state for the subsequent time step defining characteristics of radiation to be emitted by the radiation delivery apparatus in the subsequent time step.

Another non-limiting aspect of the invention provides a method for delivering radiation dose to a patient using a radiation delivery apparatus. The method comprises: providing a radiation delivery apparatus comprising a radiation source and one or more moveable elements; defining a machine state, the machine state comprising positions of the one or more moveable elements and wherein, when the radiation source is active, the machine state defines characteristics of radiation emitted by the radiation delivery apparatus; for each of a plurality of time steps in a radiation delivery fraction: receiving, at an artificial intelligence (AI) agent comprising a processor configured to execute software instructions: a set of observations regarding the machine state and regarding geometry of the patient; determining, by the AI agent, a current treatment state of the patient based at least in part on the set of observations; determining, by the AI agent, a next action comprising a next machine state for a subsequent time step based at least in part on the current treatment state and an artificial intelligence (AI) policy determined a priori using a machine-learning process executed on training data, the next machine state for the subsequent time step defining characteristics of radiation to be emitted by the radiation delivery apparatus in the subsequent time step; and causing the apparatus to perform the next action to thereby achieve the next machine state in the subsequent time step.

Another non-limiting aspect of the invention provides a system for determining radiation dose to deliver to a patient using a radiation delivery apparatus. The system comprises: a radiation delivery apparatus comprising a radiation source and one or more moveable elements; and an artificial intelligence (AI) agent comprising a processor configured to execute software instructions. The AI agent is operable, through the output of one or more sensors, to define a machine state, the machine state comprising positions of the one or more moveable elements and wherein, when the radiation source is active, the machine state defines characteristics of radiation emitted by the radiation delivery apparatus. The AI agent is configured, for each of a plurality of time steps in a radiation delivery fraction, to: receive, a set of observations regarding the machine state and regarding geometry of the patient; determine a current treatment state of the patient based at least in part on the set of observations; determine a next action comprising a next machine state for a subsequent time step based at least in part on the current treatment state and an artificial intelligence (AI) policy determined a priori using a machine-learning process executed on training data, the next machine state for the subsequent time step defining characteristics of radiation to be emitted by the radiation delivery apparatus in the subsequent time step.

Another non-limiting aspect of the invention provides a system for delivering radiation dose to a patient. The system comprises: a radiation source; one or more moveable elements; and an artificial intelligence (AI) agent comprising a processor configured to execute software instructions. The AI agent is configured to: define a machine state, the machine state comprising positions of the one or more moveable elements and wherein, when the radiation source is active, the machine state defines characteristics of radiation emitted by the radiation delivery apparatus; and for each of a plurality of time steps in a radiation delivery fraction: receive a set of observations regarding the machine state and regarding geometry of the patient; determine a current treatment state of the patient based at least in part on the set of observations; determine a next action comprising a next machine state for a subsequent time step based at least in part on the current treatment state and an artificial intelligence (AI) policy determined a priori using a machine-learning process executed on training data, the next machine state for the subsequent time step defining characteristics of radiation to be emitted by the radiation delivery apparatus in the subsequent time step; and cause the apparatus to perform the next action to thereby achieve the next machine state in the subsequent time step.

Another non-limiting aspect of the invention provides a method for delivering radiation dose to a patient. The method comprises providing a machine, the machine comprising: a radiation source; a plurality of moveable aperture-defining elements whose positions, in combination, define an aperture through which radiation from the radiation source may pass; and a moveable gantry arm on which the radiation source and the plurality of aperture-defining elements are disposed. The method further comprises defining a machine state, the machine state comprising: an intensity of the radiation source; a position of each of the plurality of moveable aperture-defining elements; and a position of the moveable gantry. The method further comprises, for each of a plurality of time intervals in a radiation delivery fraction:

receiving at an artificial intelligence (AI) agent comprising a processor configured to execute software instructions, a set of observations representing sensed information about the machine state and a patient state; determining, by the AI agent and based at least in part on the set of observations, a current treatment state; determining, by the AI agent, a next action comprising a next machine state for a subsequent time interval based at least in part on the current treatment state and an artificial intelligence (AI) policy determined using previously processed training data; and causing the machine to perform the next action to thereby achieve the next machine state in a subsequent time interval.

Another non-limiting aspect of the invention provides an apparatus for delivering radiation dose to a patient. The apparatus comprises: a machine comprising: a radiation source; a plurality of moveable aperture-defining elements whose positions, in combination, define an aperture through which radiation from the radiation source may pass; and a moveable gantry arm on which the radiation source and the plurality of aperture-defining elements are disposed. The apparatus further comprises an artificial intelligence (AI) agent comprising a processor configured to execute software instructions. The AI agent is configured to define a machine state, the machine state comprising: an intensity of the radiation source; a position of each of the plurality of moveable aperture-defining elements; and a position of the moveable gantry. The AI agent is further configured to, for each of a plurality of time intervals in a radiation delivery fraction: receive at an artificial intelligence (AI) agent, a set of observations representing sensed information about the machine state and a patient state; determine, based at least in part on the set of observations, a current treatment state; determine a next action comprising a next machine state for a subsequent time interval based at least in part on the current treatment state and an artificial intelligence (AI) policy determined using previously processed training data; and cause the machine to perform the next action to thereby achieve the next machine state in a subsequent time interval.

Another non-limiting aspect of the invention provides a method for training an artificial intelligence (AI) agent using machine learning for delivering radiation dose to a patient. The method comprises: receiving a set of clinical goals; determining a reward function based at least in part on the set of clinical goals; determining an artificial intelligence (AI) policy; providing a simulated radiation delivery apparatus comprising a simulated radiation source and one or more simulated moveable elements, wherein a simulated machine state is defined by a simulated intensity of the simulated radiation source and simulated positions of the one or more simulated moveable elements, the machine state defining characteristics of simulated radiation emitted by the radiation delivery apparatus. The method further comprises, for each of a plurality of time steps in a simulated radiation delivery fraction: receiving at the AI agent, a set of observations representing simulated sensed information about the simulated machine state and a simulated patient state; determining, based at least in part on the set of observations, a current simulated treatment state; updating the AI policy based at least on a current reward wherein the current reward is evaluated based on the current simulated treatment state and the reward function; determining, by the AI agent, a next action comprising a next simulated machine state for a subsequent time step based at least in part on the current simulated treatment state and the AI policy; and causing the simulated radiation delivery apparatus to perform the next action to thereby achieve the next simulated machine state in a subsequent time step.

Another non-limiting aspect of the invention provides a method for training an artificial intelligence (AI) agent using machine learning for delivering radiation dose to a patient. The method comprises: receiving a set of clinical goals; determining a reward function based at least in part on the set of clinical goals; determining an artificial intelligence (AI) policy; providing a simulated machine, the simulated machine comprising: a simulated radiation source; a plurality of simulated moveable aperture-defining elements whose positions, in combination, define an aperture through which radiation from the simulated radiation source may pass; and a simulated moveable gantry arm on which the simulated radiation source and the plurality of simulated aperture-defining elements are disposed; defining a simulated machine state, the simulated machine state comprising: an intensity of the simulated radiation source; a position of each of the plurality of simulated moveable aperture-defining elements; and a position of the simulated moveable gantry. The method further comprises, for each of a plurality of time steps in a simulated radiation delivery fraction: receiving at the AI agent, a set of observations representing simulated sensed information about the simulated machine state and a simulated patient state; determining, based at least in part on the set of observations, a current simulated treatment state; updating the AI policy based at least on a current reward wherein the current reward is evaluated based on the current simulated treatment state and the reward function; determining, by the AI agent, a next action comprising a next simulated machine state for a subsequent time step based at least in part on the current simulated treatment state and the AI policy; and causing the simulated machine to perform the next action to thereby achieve the next simulated machine state in a subsequent time step.

The one or more moveable elements may comprise one or more of: a plurality of aperture-defining elements whose positions, in combination define an aperture through which radiation from the radiation source is directable; a radiation source-moving element whose position defines an orientation at which radiation from the radiation source is directable.

Determining, by the AI agent, the current treatment state of the patient based at least in part on the set of observations may comprise determining that there is a preceding time step in the radiation delivery fraction and determining, by the AI agent, the current treatment state of the patient based at least in part on a preceding treatment state of the patient determined as part of the preceding time step. Determining, by the AI agent, the current treatment state of the patient based at least in part on the set of observations may comprise determining that there is no preceding time step in the radiation delivery fraction and that the patient has been subjected to radiation treatment in previous radiation delivery fraction and determining, by the AI agent, the current treatment state of the patient based at least in part on a preceding treatment state determined at a conclusion of the previous radiation delivery fraction. Determining, by the AI agent, the current treatment state of the patient based at least in part on the set of observations may comprise determining that there is no preceding time step in the radiation delivery fraction and that the patient has not been subjected to radiation treatment in previous radiation delivery fraction and determining, by the AI agent, the current treatment state of the patient based at least in part on defining an initial treatment state.

Defining an initial treatment state may comprises at least one of: defining patient geometry based on image data taken from the patient prior to delivery of radiation; instantiating in memory a variable representing an accumulated treatment time initialized to a value of zero; and instantiating in memory a variable representing a cumulative delivered dose initialized to a value of zero.

It may be determined that there is no preceding time step in the radiation delivery fraction and that the patient has been subjected to radiation treatment in previous radiation delivery fraction in which case the methods and systems may comprise determining, by the AI agent, the current treatment state of the patient based at least in part on patient geometry determined using image data taken from the patient after the previous radiation delivery fraction.

The current treatment state of the patient may comprise estimated geometries of voxels of interest within the patient's body, the estimated geometries may be based at least in part on the observations regarding the geometry of the patient. The voxels of interest may comprise at least one of: voxels corresponding to target tissue; and voxels corresponding to one or more of the organs of the patient.

The methods and systems may comprise determining, by the AI agent, the estimated geometries based at least in part on the observations regarding the geometry of the patient and one or more models of patient movement. The one or more models of patient movement may comprise a model of changes in patient geometry due to respiration. The one or more models of patient movement may comprise a model which predicts changes in geometry of voxels in an interior of the patient's body based on change in geometry an exterior of the patient's body.

The one or more models of patient movement may be based at least in part a plurality of images of the patient obtained over a period of time prior to the radiation delivery fraction. The one or more models of patient movement may be based on correlations between a reference motion model and the plurality of images of the patient obtained over the period of time. The one or more models of patient movement may comprise a population-based model based on a population that does not include the patient.

Determining the current treatment state of the patient may comprise determining an estimated cumulative dose absorbed by target tissue during the radiation delivery fraction.

Determining the current treatment state of the patient may comprise: updating a 3D image reconstruction of volumes of interest within the patient's body based on the observations regarding the geometry of the patient; transforming a cumulative dose absorbed by the target tissue in a preceding time step to the updated 3D image reconstruction; and estimating an additional dose delivered to the target tissue at a current time step based at least on the updated 3D image reconstruction, the observations regarding the machine state at the current time step, and a dose estimation engine. Determining the estimated cumulative dose absorbed by the target tissue during the radiation delivery fraction may comprise determining a sum of the transformed cumulative dose from the preceding time step and the additional dose.

Determining the current treatment state of the patient may comprise determining an estimated cumulative dose absorbed by a non-target organ of the patient during the radiation delivery fraction. Determining the estimated cumulative dose absorbed by the non-target organ of the patient during the radiation delivery fraction may comprise determining that the estimated cumulative dose absorbed by the non-target organ of the patient during the radiation delivery fraction exceeds a fractional threshold for the non-target organ and the method comprises determining the next action comprising the next machine state for the subsequent time step to comprising terminating irradiation of the patient for the radiation delivery fraction.

Determining the current treatment state of the patient may comprise determining an accumulated treatment time during the radiation delivery fraction.

The AI policy may comprise a mapping. Determining, by the AI agent, the next action comprising the next machine state for the subsequent time step may comprise creating a correspondence from the current treatment state to the next action using the mapping.

The mapping, in creating the correspondence from the current treatment state to the next action, may be based on maximizing a reward function which maximizes a cumulative reward obtained over all expected subsequent time steps.

The methods or systems may comprise imposing on the AI agent, at each of the plurality of time steps in the radiation delivery fraction, a set of one or more constraints, the set of one or more constraints limiting a space of options available to the AI agent for determining the next action. The set of one or more constraints may comprise any one or more of: a maximum distance that the radiation source may travel between a current time step and the subsequent time step; maximum distances that the one or more moveable elements may travel between the current time step and the subsequent time step; a maximum change in the intensity of the radiation source between the current time step and the subsequent time step; and a maximum value in the intensity of the radiation source.

The methods or systems may comprise training the AI agent to determine the AI policy using a reinforcement based machine-learning process together with the training data.

The methods or systems may comprise defining an initial treatment state, wherein: if there is a preceding time step in the radiation delivery fraction, defining the current treatment state is based at least in part on a preceding treatment state of the preceding time step in the delivery fraction; if there is no preceding time step in the radiation delivery fraction and there exists a preceding fraction, defining the current treatment state is based at least in part on a preceding treatment state of the preceding fraction; and if there is no preceding time step in the radiation delivery fraction and there is no preceding fraction, defining the current treatment state is based at least in part on the initial treatment state.

Determining the current treatment state may comprise determining a cumulative dose absorbed by a target volume during the radiation delivery fraction and an accumulated treatment time during the radiation delivery fraction.

Determining the current treatment state may comprise: updating 3D image reconstructions of volumes of interest; updating delineations of the volumes of interest in the 3D image reconstructions; transforming a cumulative dose absorbed by the target volume in a preceding time step to the 3D image reconstructions; and calculating an additional dose delivered to the target volume at a current time step based on at least the 3D image reconstructions, the set of observations about the machine state at the current time step, and a dose calculation engine. The cumulative dose may comprise a sum of the cumulative dose in a preceding time step and the additional dose.

Transforming the cumulative dose to the 3D image reconstructions and calculating the additional dose delivered to the target volume may each comprise updating a dose matrix.

Determining the next action by the AI agent may be based at least in part on an evaluation of whether the cumulative dose absorbed by the volume of interest during the radiation delivery fraction has exceeded a target fractional dose. If the cumulative dose absorbed by the target volume during the radiation delivery fraction has exceeded the target fractional dose, the next action may comprise issuance of a stop command and causing the machine (apparatus) to perform the next action comprises setting the intensity of the radiation source to zero.

The initial treatment state may comprise instantiating in memory a variable representing an accumulated treatment time initialized at a value of zero, and a variable representing a cumulative delivered dose initialized at a value of zero.

The AI policy may comprise a mapping and determining the next action may comprise the AI agent creating a correspondence from the current treatment state to the next action using the mapping. The mapping, in creating a correspondence from the current treatment state to the next action, may rely in part on a function which maximizes a cumulative reward obtained over all subsequent time steps.

The methods or systems may comprise providing a couch for accommodating a patient during the delivery of radiation dose, the machine state comprising a position of the couch.

The methods or systems may comprise providing a patient motion model representing expected variation in the geometry of volumes of interest within the patient. Providing the patient motion model may comprise analysis of a plurality of images obtained of the patient prior to the radiation delivery fraction. Providing the patient motion model may comprise correlating a reference motion model to one or more images obtained of the patient prior to the radiation delivery fraction.

The methods or systems may comprise determining, at each of the plurality of time steps in the radiation delivery fraction, an estimated patient motion at a current time step based at least in part on prior patient motion from one or more preceding time steps and the patient motion model. The treatment state may comprise data representing the prior patient motion from the one or more preceding time steps.

The methods or systems may comprise evaluating, at each of the plurality of time steps in the radiation delivery fraction, whether the estimated patient motion exceeds a motion management threshold, and if the estimated patient motion is evaluated to exceed the motion management threshold, indicating a requirement for active motion management in one or more of the patient state and the current treatment state. The motion management threshold may be around 3 mm.

The estimated patient motion may comprise an aggregate value representing overall motion in a plurality of points in the volumes of interest. Motion in volumes of interest in a direction defined by a beam's-eye-view of the radiation source may be assigned a lower weight compared to motion in volumes of interest in a direction transverse to the beam's-eye-view in determining the aggregate value of estimated patient motion.

The patient motion may describe a cyclic motion of volumes of interest due to a respiratory cycle of the patient.

The methods or systems may comprise imposing on the AI agent, at each of the plurality of time steps in the radiation delivery fraction, a set of one or more constraints, the set of one or more constraints limiting a space of options available to the AI agent for determining the next machine state. The set of one or more constraints may comprise one or more of: a maximum distance that the radiation source may travel between a current time step and a subsequent time step; a maximum distance that each of the plurality of moveable aperture-defining elements may move between the current time step and the subsequent time step; a maximum change in the intensity of the radiation source between the current time step and the subsequent time step; and a maximum value in the intensity of the radiation source.

Imposing the set of one or more constraints to the AI agent may cause continuous motion of the machine between a current time step and a subsequent time step.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Aspects of the invention relate to the planning and delivery of radiation treatments by modalities which involve moving a radiation source along a trajectory relative to a subject while delivering radiation to the subject. An artificial intelligence (AI) agent trained using reinforcement learning (and/or some other suitable form of machine learning) is used to control the radiation delivery parameters in effort to achieve desired delivery of radiation therapy. In some embodiments, the AI agent selects suitable control steps (e.g. radiation delivery parameters for particular time steps), while accounting for patient motions, difference(s) in patient anatomical geometry and/or the like.

Figures 1, 1A:
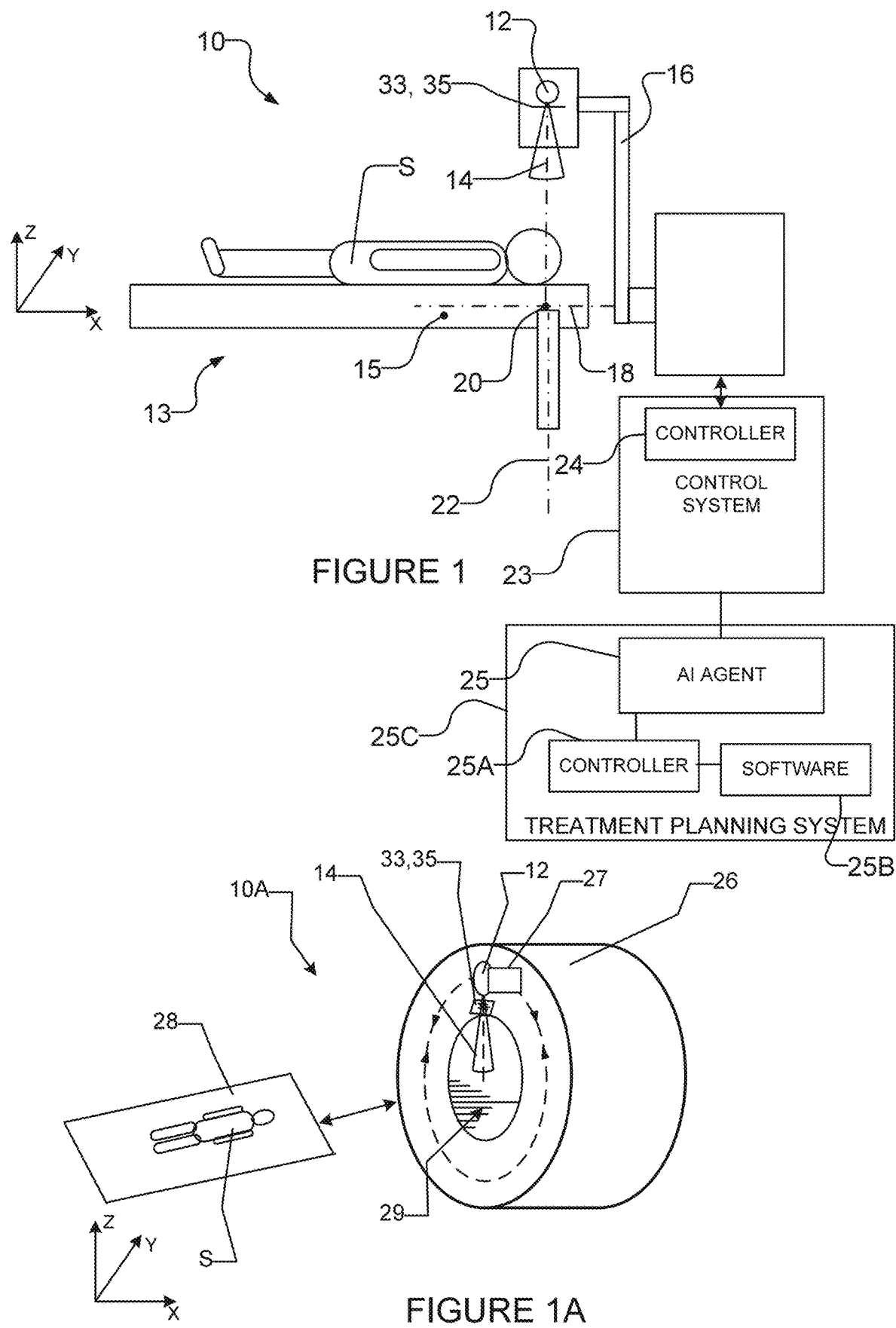
FIG. 1 is a schematic view of an exemplary radiation delivery apparatus in conjunction with which embodiments the invention may be practised.
FIG. 1A is a schematic view of another exemplary radiation delivery apparatus in conjunction with which embodiments of the invention may be practised.

FIG. 1 shows an example radiation delivery apparatus 10 comprising a radiation source 12 capable of generating or otherwise emitting a beam 14 of radiation. Radiation source 12 may comprise a linear accelerator, for example. A subject S is positioned on a table or "couch" 15 which can be placed in the path of beam 14. Apparatus 10 comprises movable parts that permit the location of radiation source 12 and orientation of radiation beam 14 to be moved relative to subject S. These parts may be referred to collectively as a beam positioning mechanism 13.

In the illustrated radiation delivery apparatus 10, beam positioning mechanism 13 comprises a gantry 16 which supports radiation source 12 and which can be rotated or pivoted about an axis 18. Axis 18 and beam 14 intersect at an isocenter 20. In some embodiments, a suitable beam positioning mechanism 13 may comprise a gantry capable of moving radiation source 12 with additional or alternative degrees of freedom. Beam positioning mechanism 13 of the illustrated embodiment also comprises a moveable couch 15. In exemplary radiation delivery apparatus 10, couch 15 can be translated in any of three orthogonal directions (shown in FIG. 1 as X, Y, and Z directions) and can be rotated about an axis 22. In some embodiments, couch 15 can additionally or alternatively be rotated about one or more of its other axes. The location of source 12 and the orientation of beam 14 can be changed (relative to subject S) by moving one or more of the movable parts of beam positioning mechanism 13.

Each separately-controllable component for moving source 12 and/or orienting beam 14 relative to subject S may be termed a "motion axis". In some cases, moving source 12 or beam 14 along a particular trajectory may require motions of two or more motion axes. In the exemplary radiation delivery apparatus 10 shown in FIG. 1, motion axes include:
rotation of gantry 16 about axis 18;
translation of couch 15 in any one or more of the X, Y, Z directions; and
rotation of couch 15 about axis 22. Radiation delivery apparatus of other embodiments may include additional or alternative motion axes.

Radiation delivery apparatus 10 typically comprises a control system 23 capable of controlling the mechanical aspects of radiation delivery apparatus 10 and, optionally, the intensity of its radiation source 12. By way of non-limiting example, control system 23 may control, among other things, the movement of the motion axes of radiation delivery apparatus 10, the intensity of radiation source 12, the movement (e.g. positions and orientation) of the MLC leaves (described in more detail below), movement of the MLC jaws (described in more detail below) and/or the like. Control system 23 may generally comprise hardware components and/or software components. In the illustrated embodiment, control system 23 comprises a controller 24 capable of executing software instructions. For example, control system 23 is preferably capable of receiving (as input) a set of desired parameters (e.g. positions and/or orientations) for its motion axes and, responsive to such input, controllably moving one or more of its motion axes to achieve the set of desired motion axes parameters. Similarly, control system 23 may also receive as input, instructions about other radiation delivery parameters. By way of non-limiting example, such other radiation delivery parameters may include: the intensity of radiation source 12; one or more parameters of a beam-shaping mechanism 33 (e.g. parameters corresponding to the movement, positions and/or orientations of MLC leaves and/or MLC jaws) described in more detail below; and/or the like. In response to such input, control system 23 may cause radiation delivery apparatus 10 to effect the corresponding radiation delivery parameters.

While radiation delivery apparatus 10 represents a particular type of radiation delivery apparatus in conjunction with which the invention may be implemented, it should be understood that the invention may be implemented on different radiation delivery apparatus which may comprise different motion axes and/or different sets of radiation delivery parameters. In general, embodiments of the invention may be implemented in conjunction with any set of motion axes that can create relative movement between a radiation source 12 and a subject S, from a starting point along a trajectory to an ending point. In general, embodiments of the invention may be implemented in conjunction with any set of radiation delivery parameters which may be used by any such radiation delivery apparatus.

Another example of a radiation delivery apparatus 10A that provides an alternative set of motion axes is shown in FIG. 1A. In exemplary apparatus 10A, source 12 is disposed in a toroidal housing 26. A mechanism 27 permits source 12 to be moved around housing 26 to irradiate a subject S from different sides. Subject S is on a table 28 which can be advanced through a central aperture 29 in housing 26. Apparatus having configurations like that shown schematically in FIG. 1A are used to deliver radiation in a manner commonly called "Tomotherapy".

In accordance with particular embodiments of the invention, beam positioning mechanism 13 causes source 12 and/or beam 14 to move along a trajectory while radiation dose is controllably delivered to target regions within subject S. A "trajectory" is a set of one or more movements of one or more of the movable parts of beam position mechanism 13 that results in the beam position and orientation changing from a first position and orientation to a second position and orientation. The first and second positions and the first and second orientations are not necessarily different. For example, a trajectory may comprise a rotation of gantry 16 from a starting point through an angle of 360° about axis 18 to an ending point, in which case the beam position and orientation at the starting and ending points are the same.

The first and second beam positions and beam orientations may be specified by a first set of motion axis parameters (corresponding to the first beam position and the first beam orientation) and a second set of motion axis parameters (corresponding to the second beam position and the second beam orientation). As discussed above, control system 23 of radiation delivery apparatus 10 can controllably move its motion axes between the first set of motion axis parameters and the second set of motion axis parameters. In general, a trajectory may be described by more than two beam positions and beam orientations. For example, a trajectory may be specified by a plurality of sets of motion axis parameters, each set of motion axis parameters corresponding to a particular beam position and a particular beam orientation. Control system 23 can then controllably move its motion axes between each set of motion axis parameters along the trajectory. In some embodiments, an artificial intelligence (AI) agent (described in more detail below) may define the trajectory (e.g. by choosing motion axis parameters at successive control points) in each time step.

A set of motion axis parameters may make up a subset of the radiation delivery parameters corresponding to a control point. More generally, a control point may comprise (or otherwise be associated with) a set of control parameters (also referred to herein as a set of radiation delivery parameters) for a given time step. For any given control point, such control parameters may include, by way of non-limiting example: a set of motion axis parameters, one or more parameters corresponding intensity of radiation source 12, one or more parameters of a beam-shaping mechanism 33 (e.g. parameters corresponding to the movement, positions and/or orientations of MLC leaves and/or MLC jaws) described in more detail below; and/or the like. In some embodiments, during radiation delivery, a trained artificial intelligence (AI) agent (described in more detail below) may select the set of control parameters for successive control points corresponding to successive time steps. In some embodiments, the trained AI agent may define the trajectory (e.g. the locations of successive control points) in successive time steps. In some embodiments, the trajectory may be provided by some other entity (e.g. a clinician) or otherwise defined for the AI agent. In some embodiments, the locations of the control points on a trajectory may be defined by the AI agent.

In general, a trajectory may be arbitrary and is only limited by the particular radiation delivery apparatus and its particular beam positioning mechanism. Within constraints imposed by the design of a particular radiation delivery apparatus 10 and its beam positioning mechanism 13, radiation source 12 and/or beam 14 may be caused to follow an arbitrary trajectory relative to subject S by causing appropriate combinations of movements of the available motion axes.

Figure 2:
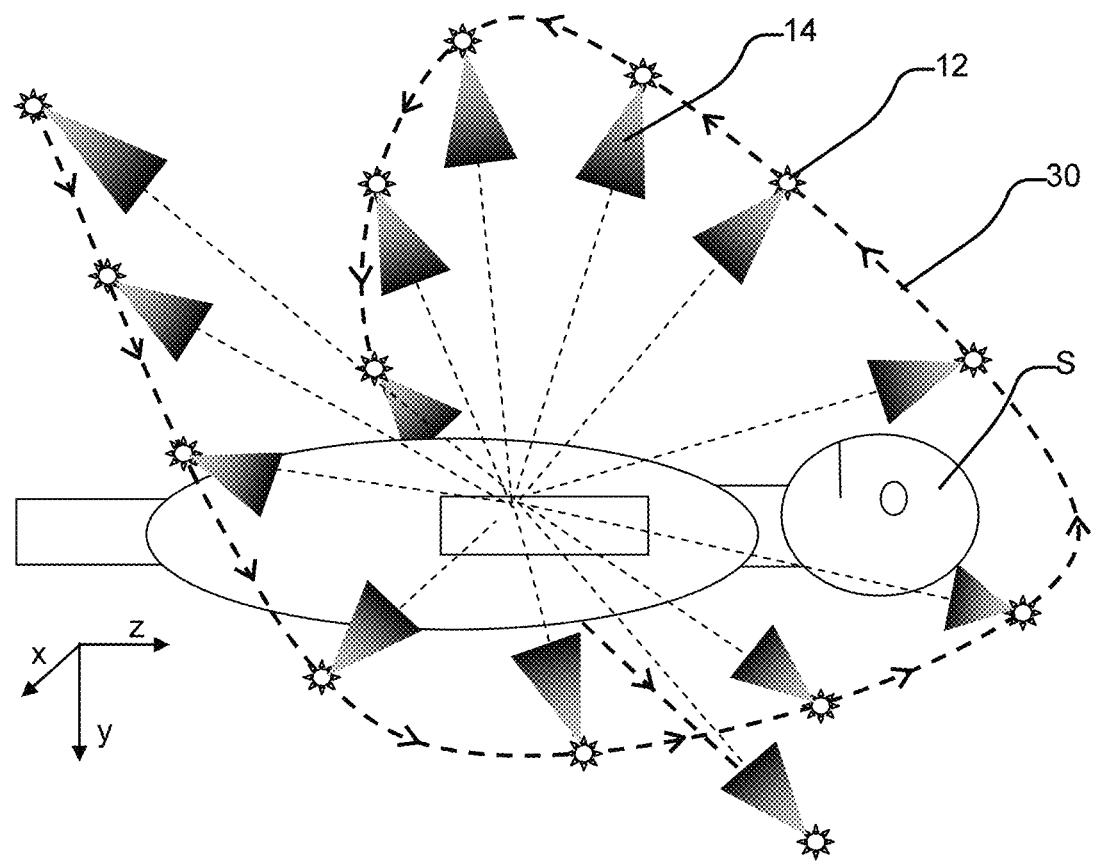
FIG. 2 is a schematic illustration of a trajectory for a radiation source according to an example embodiment.

FIG. 2 schematically depicts a radiation source 12 travelling relative to a subject S along an arbitrary trajectory 30 in three-dimensions while delivering radiation dose to a subject S by way of a radiation beam 14. The control points of the FIG. 2 trajectory are shown schematically by star-shapes and corresponding beams. The position and orientation of radiation beam 14 changes as source 12 moves along trajectory 30. In some embodiments, the changes in position and/or direction of beam 14 and/or other radiation delivery parameters may occur substantially continuously (between control points) as source 12 moves along trajectory 30. In some embodiments, such changes may occur discretely at each control point. While source 12 is moving along trajectory 30, radiation dose may be provided to subject S continuously (i.e. at all times during the movement of source 12 along trajectory 30) or intermittently (i.e. radiation may be blocked or turned off at some times during the movement of source 12 along trajectory 30). Source 12 may move continuously along trajectory 30 or may move intermittently between various positions (e.g. between control points) on trajectory 30. As discussed above, trajectory 30 may be specified by an AI agent, which may define the trajectory (e.g. locations of successive control points) in each time step.

Although trajectory 30 may be defined arbitrarily, it may be desirable, in some embodiments, that source 12 and/or beam 14 not have to move back and forth along the same path. Accordingly, in some embodiments, trajectory 30 may be constrained so that it does not overlap itself (except possibly at the beginning and end of trajectory 30). In such embodiments, the positions of the motion axes of the radiation delivery apparatus are not the same except possibly at the beginning and end of trajectory 30. In such embodiments, treatment time can be minimized (or at least reduced) by irradiating subject S only once from each set of motion axis positions.

In some embodiments, trajectory 30 may be constrained such that the motion axes of the radiation delivery device move in one direction without having to reverse directions (i.e. without source 12 and/or beam 14 having to be moved back and forth along the same path). Selection of a trajectory 30 involving movement of the motion axes in a single direction can minimize wear on the components of a radiation delivery apparatus. For example, in apparatus 10, it may be desirable to move gantry 16 in one direction, because gantry 16 may be relatively massive (e.g. greater than 1 ton) and reversing the motion of gantry 16 at various locations over a trajectory may cause strain on the components of radiation delivery apparatus 10 (e.g. on the drive train associated with the motion of gantry 16).

In some embodiments, trajectory 30 may be constrained such that the motion axes of the radiation delivery apparatus move substantially continuously (i.e. without stopping). Substantially continuous movement of the motion axes over a trajectory 30 may be preferable to discontinuous movement, because stopping and starting motion axes can cause wear on the components of a radiation delivery apparatus. In other embodiments, the motion axes of a radiation delivery apparatus may be permitted to stop at one or more locations (e.g. at discrete control points) along trajectory 30.

In some embodiments, trajectory 30 may be constrained to comprise a single, one-way, continuous 360° rotation of gantry 16 about axis 18, such that trajectory 30 overlaps itself only at its beginning and end points. In some embodiments, this single, one-way, continuous 360° rotation of gantry 16 about axis 18 may be coupled with corresponding one-way, continuous translational or rotational movement of couch 15, such that trajectory 30 is completely non-overlapping.

Figure 3A:
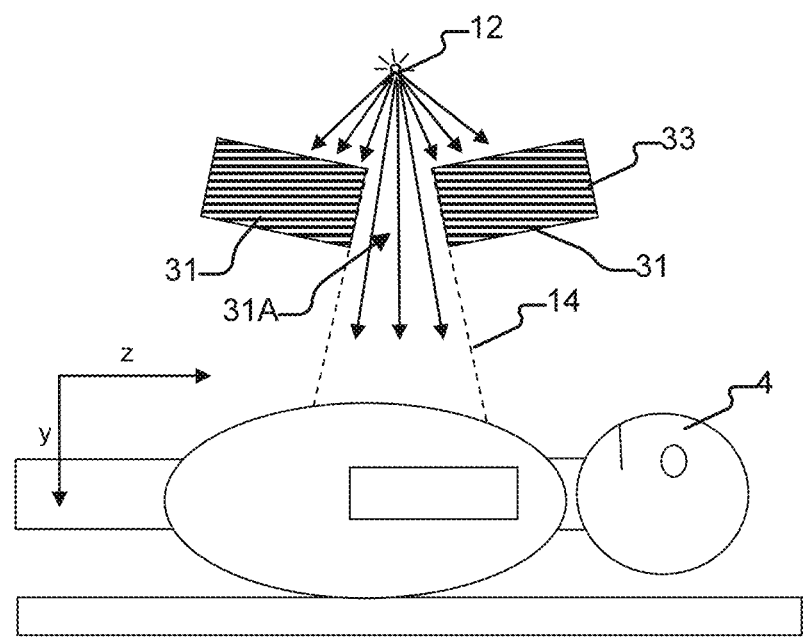
FIG. 3A is a schematic cross-sectional view of a beam-shaping mechanism according to an example embodiment.

Radiation delivery apparatus, such as exemplary apparatus 10 (FIG. 1) and 10A (FIG. 1A), typically include adjustable beam-shaping mechanisms 33 located between source 12 and subject S for shaping radiation beam 14. FIG. 3A schematically depicts a beam-shaping mechanism 33 located between source 12 and subject S. Beam-shaping mechanism 33 may comprise stationary and/or movable metal components 31. Components 31 may define an aperture 31A through which portions of radiation beam 14 can pass. Aperture 31A of beam-shaping mechanism 33 defines a two-dimensional border of radiation beam 14 in a plane normal to the direction of radiation from source 12 to the target volume in subject S (e.g. normal to the BEV). Control system 23 is preferably capable of controlling the configuration of beam-shaping mechanism 33.

Figure 3B:
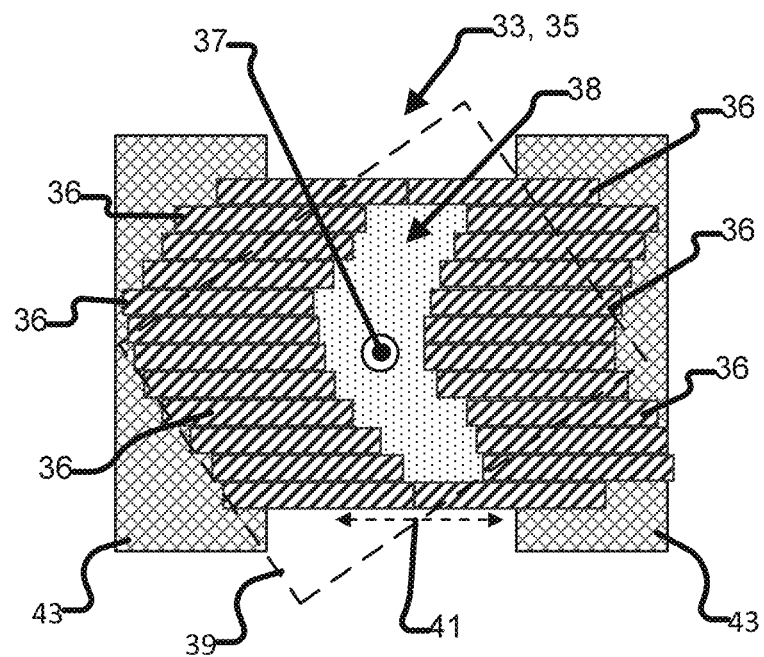
FIG. 3B is a schematic beam's eye plan view of a multi-leaf collimator-type beam-shaping mechanism according to a particular embodiment.

One non-limiting example of an adjustable beam-shaping mechanism 33 comprises a multi-leaf collimator (MLC) 35 located between source 12 and subject S. FIG. 3B schematically depicts a suitable MLC 35. As shown in FIG. 3B, MLC 35 comprises a number of leaves 36 that can be independently translated into or out of the radiation field to define one or more apertures 38 through which radiation can pass. Leaves 36, which may comprise metal components, function to block radiation. In the illustrated embodiment, leaves 36 are translatable in the directions indicated by double-headed arrow 41. The size(s) and shape(s) of aperture(s) 38 may be adjusted by selectively positioning each leaf 36.

As shown in the illustrate embodiment of FIG. 3B, leaves 36 are typically provided in opposing pairs. MLC 35 is typically mounted so that it can be rotated to different orientations about an axis 37 that extends perpendicular to a plane of leaves 36 (e.g. in a BEV direction). In the illustrated embodiment of FIG. 3B, axis 37 extends into and out of the page and dashed outline 39 shows an example of an alternate orientation of MLC 35 about axis 37.

In some embodiments, in addition to MLC leaves 36, beam-shaping mechanism 33 may optionally comprise MLC jaws 43. MLC jaws 43 may comprise a pair of opposably movable radiation blocking metal jaws, which may be thicker than that of MLC leaves 36 and which may be located to define the exterior perimeter of the aperture definable by MLC leaves 35. In some embodiments, MLC jaws 43 may also be moveable in directions 41 and/or about axis 37.

A configuration of MLC 35 can be specified by a set of beam-shaping parameters, which may include, by way of non-limiting example, MLC leaf position parameters that define a position of each leaf 36, an orientation parameter that defines an orientation of MLC 35 about axis 37 and one or more MLC jaw parameters that define the positions and/or orientation of the MLC jaws 43. The control system of a radiation delivery apparatus (e.g. control system 23 of radiation delivery apparatus 10) is typically capable of controlling the positions of leaves 36, the orientation of MLC 35 about axis 37 and the locations/orientations of the MLC jaws 43 in response to receiving a suitable set of beam-shaping parameters. MLCs can differ in design details, such as the presence or absence of MLC jaws 43, the movability of MLC jaws 43, the number of leaves 36, the widths of leaves 36, the shapes of the ends and edges of leaves 36, the range of positions that any leaf 36 can have, constraints on the position of one leaf 36 imposed by the positions of other leaves 36, the mechanical design of the MLC, and the like. The invention described herein should be understood to accommodate any type of configurable beam-shaping apparatus 33 including MLCs having these and other design variations.

The configuration of MLC 35 may be changed (for example, by moving the MLC jaws 43, rotating the MLC jaws 43 about axis 37, moving the leaves 36 and/or rotating MLC 35 about axis 37) while radiation source 12 is operating and while radiation source 12 is moving about trajectory 30, thereby allowing the shape of aperture(s) 38 to be varied dynamically while radiation is being delivered to a target volume in subject S. Since MLC 35 can have a large number of leaves 36, each of leaves 36 can be placed in a large number of positions and MLC 35 can be rotated about its axis 37, MLC 35 may have a very large number of possible configurations.

Embodiments of the present invention provide methods and systems for training and/or using a suitably trained artificial intelligence (AI) agent to control the delivery of radiation treatment to a patient. The AI agent may be implemented on a computer or processor part of a treatment apparatus to execute software instructions loaded into memory. The AI agent may make observations about its environment (e.g. the state of the patient and the state of the radiation delivery apparatus) and, based on such observations together with its training, the AI agent may autonomously act to provide instructions (e.g. suitable radiation delivery parameters_ to the delivery apparatus to deliver radiation therapy in a manner which optimally achieves a desired treatment strategy (which may comprise a set of treatment objectives). A suitable user (e.g. an oncologist and/or suitably trained clinician) may define a set of treatment objectives which may be provided to the AI agent prior to training the AI agent. The AI agent may also be provided with one or more constraints prior to training. By way of non-limiting example, such constraints may include: limitations of the radiation delivery apparatus, limitations on a trajectory and/or what motion axes may be moved during a fraction, hard dose limitations, limitations on the temporal duration of a fraction and/or the like. Such constraints may be known a priori to the AI agent or may be input to the AI agent prior to training. Together, the set of treatment objectives and the set of constraints may be referred to herein as a treatment strategy. Then, through training using reinforcement learning and/or other methods of machine learning directed to achieving the treatment strategy, the AI agent may develop an artificial intelligence (AI) policy (also referred to herein as a "treatment policy" or, "policy", for brevity).

Figure 4:
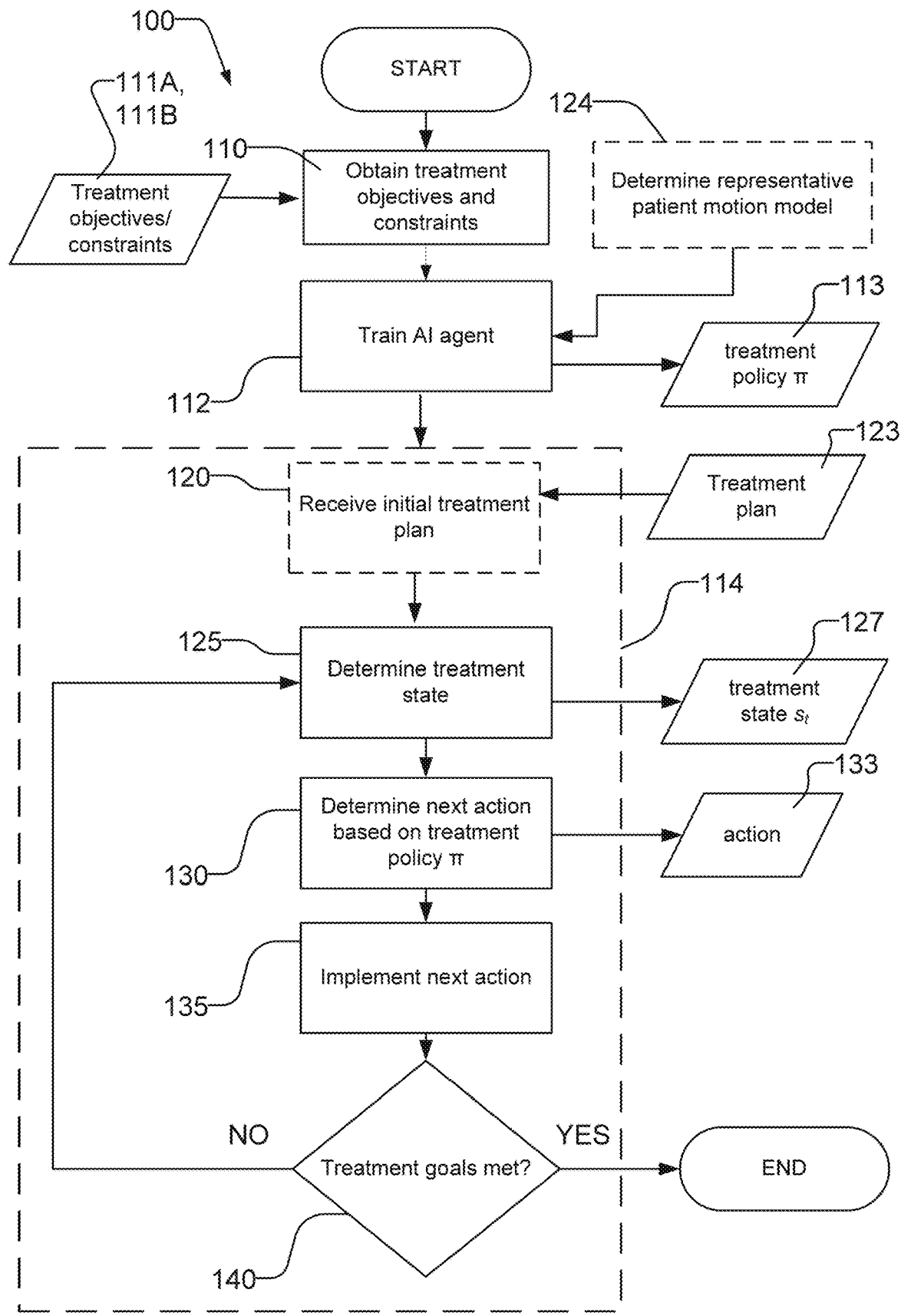
FIG. 4 is a flow chart illustrating a method of delivering radiation treatment guided by an artificial intelligence agent according to a particular embodiment of the invention.

FIG. 4 schematically depicts a radiation treatment delivery method 100 according to an example embodiment of the invention. Method 100 may be used to deliver a fractional radiation treatment. That is, there may be several fractional iterations of method 100 (each commonly referred to a fraction) which, together, provide a complete radiation treatment for a particular patient. Radiation treatment delivery method 100 may be performed, at least in part, by an artificial intelligence (AI) agent 25 and may involve: determining instructions (e.g. radiation delivery (control) parameters) at each time step over a series of time steps; providing those instructions to a radiation delivery apparatus (e.g. to controller 23 of radiation delivery apparatus 10 shown in FIG. 1); and thereby causing the radiation delivery apparatus to deliver a desired radiation dose distribution to a subject S. For ease of explanation and without loss of generality, method 100 is described in the remainder of this description for use with radiation delivery apparatus 10 shown in FIG. 1. AI agent 25 may be part of a more general treatment planning system 25C shown in FIG. 1. In the illustrated embodiment, AI agent 25 comprises its own controller 25A which is configured to execute suitable software 25B. In some embodiments, control system 23 and treatment planning system 25C (including possibly AI agent 25) may share one or more controller(s). By way of non-limiting example, treatment planning system 25C and/or AI agent 25 may be implemented by a suitably configured computer. In some embodiments, controller 25A may comprise one or more data processors, together with suitable hardware, including, by way of non-limiting example: accessible memory, logic circuitry, drivers, amplifiers, A/D and D/A converters and like. Such a controller may comprise, without limitation, a microprocessor, a computer-on-a-chip, the CPU of a computer or any other suitable data processor and/or microcontroller. Controller 25A may comprise a plurality of data processors.

Method 100 starts in block 110. In block 110, method 100 involves obtaining one or more treatment objectives 111A to be met through the delivery of radiation treatment by method 100; and, optionally, one or more constraints 111B associated with the radiation delivery. The block 110 treatment objectives 111A and/or constraints 111B may be obtained in any suitable manner. The treatment objectives 111A and/or constraints 111B obtained in block 110 may be inputs to method 100. For example, such treatment objectives 111A and/or constraints 111B may be determined by a clinician or doctor (possibly using the assistance of some computer-based system) and provided as input to method 100. The treatment objectives 111A and/or constraints 111B obtained in block 110 may be determined as a part of block 110. For example, treatment planning system 25C may comprise suitable software which allows a clinician or doctor to create and/or estimate the block 110 treatment objectives 111A and/or constraints 111B using a suitable user interface.

The block 110 treatment objectives 111A may comprise treatment objectives for the particular fraction being delivered as part of method 100 and/or treatment objectives 111A for the entire treatment, which may then be divided (e.g. by treatment planning system 25C and/or by a clinician) into the treatment objectives 111A for the particular fraction being delivered as part of method 100. The treatment objectives 111A obtained in block 110 may comprise, for example, a desired dose distribution, which may in turn comprise: desired amount(s) of radiation dose (e.g. desired minimum dose amounts) to be delivered to voxels in a target volume; and desired maximal amounts of radiation dose to be delivered to voxels corresponding to healthy tissue and/or organs. The block 110 treatment objectives 111A may additionally or alternatively comprise other treatment objectives. By way of non-limiting example, other treatment objectives 111A may comprise: a desired uniformity of dose distribution in the voxels corresponding to a target volume; a desired precision with which the dose distribution in the target volume should match a desired dose amount; a maximum time required to deliver the radiation treatment based on an individual patient's ability to stay still during treatment; priorities or weights for different treatment objectives and/or the like.

Some treatment objectives 111A may be based on so-called dose-volume histograms, which map percentages of particular volumes of tissue (e.g. a volume corresponding to a target cancer or to a healthy organ) that receive particular amounts of dose (or estimated dose). By way of specific and non-limiting examples, a dose-volume histogram based treatment objective 111A may have a form along the lines of: "the percentage volume of critical organ X receiving dose Y should be less than Z"; "the percentage volume of a target volume A receiving dose B should be greater than C"; "the maximum dose covering Z percent of critical organ X should be Y"; "the minimum dose covering C percent of target volume A should be B"; and/or the like. In general, the block 110 treatment objectives 111A may have any of a variety of different forms. By way of non-limiting example, a biological model may be used in the computation of a metric which estimates a probability that a specified dose distribution will control a disease from which the subject is suffering and/or the probability that a specified dose delivered to non-diseased tissue may cause complications. Such biological models are known as radiobiological models. The block 110 treatment objectives 111A may be based in part on one or more radiobiological models.

Block 110 may optionally also involve obtaining one or more treatment constraints 111B, to the extent that such constraints are not already known to AI agent 25. In some embodiments, some treatment constraints 111B may be hard-coded into AI agent 25, set up during calibration of AI agent 25 for use with a particular radiation delivery apparatus and/or the like. Such block 110 treatment 111B constraints may comprise hard constraints (e.g. hard constraints which define or limit the search space of possible actions) and/or soft constraints (e.g. which may manifest themselves as terms in a reward function). Such treatment constraints 111B may comprise, for example, constraints related to physical limitations of a particular radiation delivery apparatus 10. By way of non-limiting example, such treatment constraints 111B may comprise: movement (position, velocity and/or acceleration) constraints of a gantry 12, couch 15 and/or other components/axes of a radiation treatment apparatus 10; the desirability of keeping the components (e.g. gantry 12) of radiation delivery apparatus 10 moving; minimum and/or maximum radiation intensity that may be output by a radiation source; and/or the like. In some embodiments, the block 110 constraints 111B may be inherent in the radiation delivery apparatus to be used to deliver radiation and may be predetermined or hard-coded into method 100. In some embodiments, a user (e.g. a clinician) may introduce one or more block 110 constraints 111B. For example, a clinician may specify that only one or more particular movement axes of the radiation delivery apparatus may be used for the fractional treatment.

Method 100 then proceeds to block 112, where AI agent 25 is trained, using one or more machine-learning techniques, to develop and determine a treatment policy 113, π (also referred to herein as artificial intelligence policy 113, π or AI policy 113, it) which guides the decision making process of AI agent 25 during radiation delivery. AI agent 25 may be trained in block 112 according to a reinforcement learning technique, where AI agent 25 learns to take actions a based on some notion of cumulative reward. Block 112 may involve the use of any suitable reinforcement learning technique or algorithm. Non-limiting examples of suitable reinforcement learning algorithms include: Monte Carlo techniques, Q-learning techniques, SARSA (state-action-reward-state-action) techniques, deep Q-network techniques and/or the like. In some embodiments, block 112 may additionally or alternatively use one or more other suitable machine learning techniques to train AI agent 25 and to thereby develop a suitable treatment policy 113, it.

In one specific embodiment based on reinforcement learning, block 112 involves the use of reinforcement learning so that AI agent 25 can develop ("learn") an treatment policy 113, π wherein AI agent 25 will receive, as input, observations of the AI agent's environment in current and/or past time steps to ascertain a "treatment state" s at any given time step (either during treatment or during training) and will map the treatment state to a preferred action a in the next time step. For brevity, this description refers to "actions" of AI agent 25. Such references to AI agent actions may comprise AI agent 25 providing instructions (e.g. radiation delivery parameters corresponding to a preferred action to be performed by a radiation delivery system) to the radiation delivery system and then the radiation delivery system actually performing the action.

The treatment state s of a patient (including the environment in which AI agent 25 operates (e.g. observable or estimatable variables in the current radiation treatment session)) may be defined as a Markov state, although this is not necessary. A Markov state s is a state where all of the history (e.g. the treatment history of the patient) is incorporated into the current state s or, in other words, future states are independent of historical states given a current state s. In some embodiments, the block 112 training of AI agent may be implemented using reinforcement learning technique which may be modelled as a Markov decision process (MDP). In a MDP, given a current treatment state s (e.g. in a current time step), the probability $P_a(s,s')$ represents the probability that the treatment state transitions into a new state s' (e.g. at the conclusion of the next time step) upon AI agent 25 taking an action â (i.e. providing a set of radiation delivery parameters which are executed by radiation delivery apparatus 10). The transition of treatment state S into the new treatment state s' may be described as a stochastic process stemming from a number of stochastic variables. Non-limiting examples of variables that may be modelled stochastically include: differences between the amount of radiation delivered from the radiation source and the amount of radiation absorbed by tissue, non-uniformity of the dose absorbed by tissue, susceptibility of different tissues to radiation, unexpected adverse patient reaction to a received dose of radiation, patient movement, set up errors and/or the like. Where treatment state observations are modelled as stochastic processes, AI agent 25 may generate stochastic treatment policies it, which specify the probability, π(a|s), for taking an action a in each state S.

Treatment policy 113, π of AI agent 25 may be based on optimizing (e.g. maximizing) cumulative expected reward E[R]. The cumulative expected reward E[R] may also be referred to as the expected return E[R], where the return R is defined as a sum of future discounted rewards $R=\Sigma_{t=0}^{\infty}\gamma^t r_t$ where $r_t$ is the reward at time step t and $\gamma \in [0,1]$ is the discount rate for rewards occurring in the future. The reward $r_t$ at any time step may be determined according to a reward function. The reward function may comprise a function that represents a reward metric obtained by the performance of an action a based on a current treatment state s (including, for example, observations of the current environment) and expected changes in the treatment state (including, for example, expected environment changes) stemming from that action. Treatment policy 113, π learned by AI agent 25 in block 112 may involve maximizing the cumulative expected reward E[R]. This reward maximization problem may be subject to one or more constraints (e.g. the block 110 treatment constraints 111B).

The reward function may be based at least in part on the block 110 treatment objectives 111A, and optionally, one or more of the block 110 constraints 111B (e.g. soft constraints can be incorporated into the reward function). Basing the reward function on such treatment objectives 111A means that the reward function may reflect how clinicians evaluate the conformity to, and the success of a radiation treatment plan. A relatively high reward $r_t$ is attributed if the treatment objectives 111A obtained at block 110 are being met by the performance of the AI agent's action a at a particular time step t. Additional smaller positive rewards can be given for fulfilment of one or more of the optimization goals. Conversely, a lower reward $r_t$ can be attributed if the block 110 treatment objectives 111B are not being met by a particular action a, or if the action produces a state giving rise to future uncertainties potentially causing treatment objectives to not be met. During the block 112 training, it is possible for an oncologist or clinician to interfere with the training process to provide more accurate guidance, and in doing so, alter the reward function. For example, an oncologist may provide further instructions on what kinds of dose distributions are beneficial and what kinds are detrimental.

Figure 5:
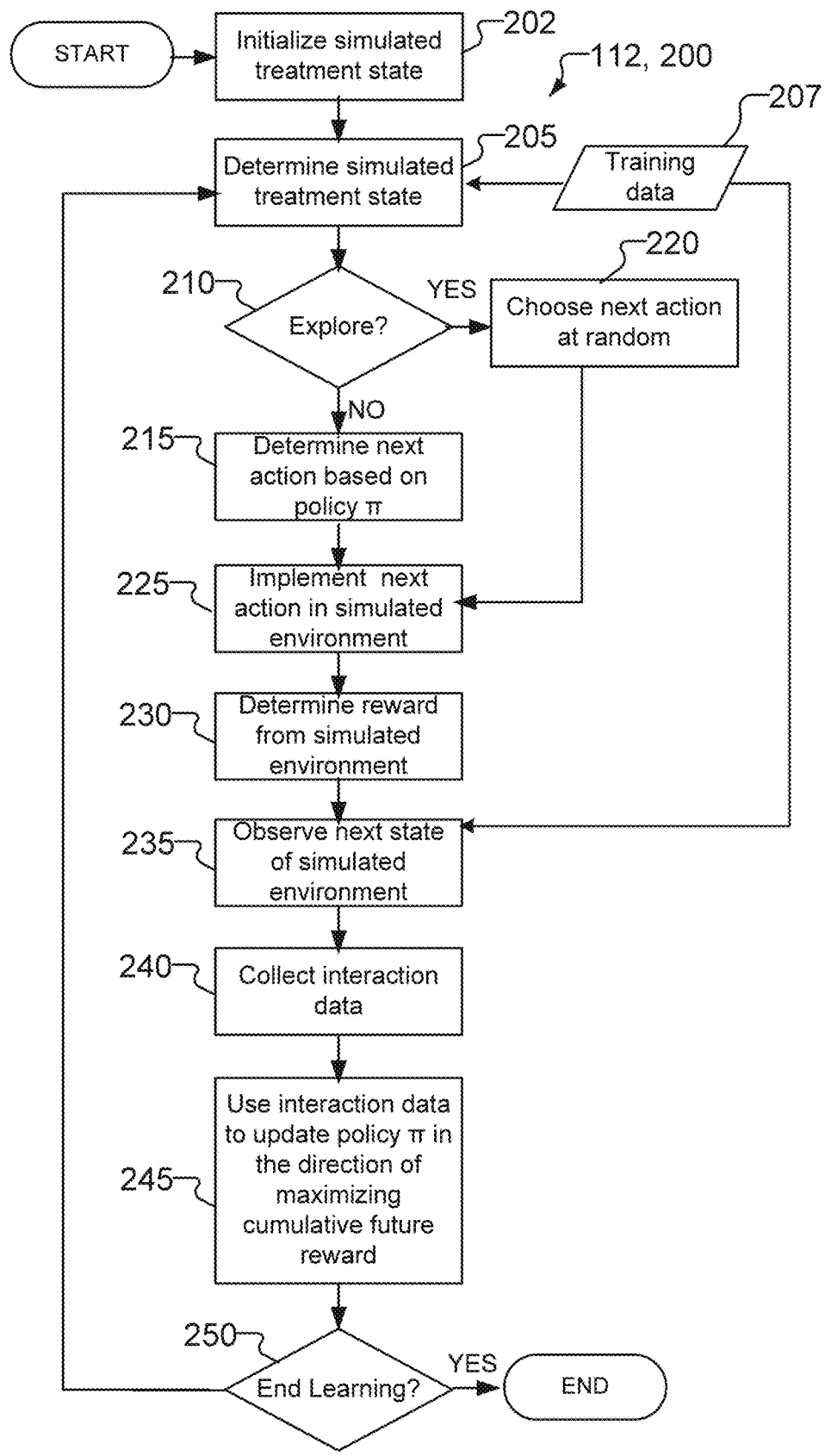
FIG. 5 is a flow chart illustrating a method of training an artificial intelligence agent using reinforcement learning according to a particular embodiment of the invention.

FIG. 5 schematically depicts a machine learning method 200 that may be used in block 112 to train AI agent 25 in accordance with a particular embodiment. Machine learning method 200 depicted in the particular exemplary embodiment of FIG. 5 is a reinforcement learning method 200, although other machine learning techniques could be used in other embodiments. In some embodiments, method 200 may be performed in whole or in part based on a simulated representation of a patient to be treated in method 100 (FIG. 4). For example, the simulated environment used in method 200 may be based on a simulation of the actual patient being treated in method 100 (FIG. 4). By way of non-limiting example, the simulated environment used in training method 200 may incorporate data (e.g. CT scans, other images, ECG measurements, respiratory measurements and/or the like) that are taken directly from the patient being treated in method 100 and/or models whose parameters are based on such data that is specific to the patient being treated in method 100. In some embodiments, some or all of the data used to implement the training method 200 may be taken from data from other individuals and/or from population-based data and/or models, whose parameters are based on such data.

Some issues that are desirable to address using machine learning based treatment include patient motion during treatment, changes in patient anatomical geometry (e.g. between fractions, between imaging and treatment and/or during treatment) and/or other changes in patient geometry. Unless the context dictates otherwise, such movement and geometrical changes may be collectively referred to herein as changes in patient geometry. In some embodiments, the simulated environment used in machine-learning method 200 comprises models and/or the like for how patient geometry may change between fractions, between imaging and treatment and/or during treatment. Such patient geometry models could include, without limitation, a model for the particular patient based in whole or in part off of measurements taken from the particular patient. For example, such a model for movement associated with respiration could be based on 4D-CT capturing the patient's respiratory motion. Such patient geometry simulation could be based, without limitation, in whole or in part on a library of motion models observed in a population of patients. For example, motion models may be used to simulate the changes in a patient's anatomical geometry if the patient's body weight decreases by 10% between imaging and delivery of a particular fraction. A simulated environment could additionally or alternatively comprise algorithmic techniques for creating new motion model candidates (such as, by way of non-limiting example, a generative neural network).

Returning now to FIG. 5, method 200 starts in block 202 where a simulated treatment state of a patient is initialized. In some embodiments, the treatment state may be implemented as a suitable data structure (e.g. a vector) where each element of the data structure is initialized in block 202 with a suitable value. In some embodiments, some parameters of the block 202 initialized state may be selected based on known (or obtained) data. By way of non-example, where training method 200 is based on a particular patient to be treated in method 100 (FIG. 4), block 202 may be initialized based on data taken from images of the patient (e.g. voxels containing the target tissue, voxels containing critical organs, parameters of respiratory models and/or the like), other measurements relating to the patient (e.g. ECG measurements, respiratory measurements and/or the like). In some embodiments, some parameters of the block 202 initialized state may be set to specific values and/or random values.

Method 200 then proceeds to block 205 which involves determining the simulated treatment state. The block 205 simulated treatment state may be based on training data 207. In the first iteration of method 200, the block 205 simulated treatment state may be the same as the block 202 initialization state. In subsequent, iterations, the block 205 simulated treatment state may be based (at least in part) on models of the simulated environment which may be based on training data 207, observations about the simulated environment which may be based on training data 207, possibly together with actions taken since the last implementation of block 205. Method 200 then proceeds to block 210 which involves making a decision as to whether to explore a random next action (block 210 YES branch) or to determine the next action based on an existing version of the treatment policy 113, π (block 210 NO branch). The block 210 decision may be based on a trade-off between exploration (of possible new actions—block 210 YES branch) and exploitation (of existing treatment policy 113, π which will maximize cumulative expected reward—block 210 NO branch). The block 210 exploration versus exploitation trade-off may be implemented by any suitable technique, including, by way of non-limiting example, the so-called ϵ-greedy approach, where $0<\epsilon<1$ is a parameter which controls the amount of exploration versus exploitation. For example, the probability that exploitation (block 210 NO branch) is selected in bock 210 may be set to 1−ε and the probability that exploration (block 210 YES branch) is selected in bock 210 may be set to ε. A random number in a range (0,1) may then be generated to make the block 210 decision.

In some embodiments, the value of ε may vary during the implementation of method 200. For example, the parameter ε may be set to be large at the beginning of method 200 (resulting in more YES branch (explore) decisions in block 210) and may converge to a relatively small value in subsequent iterations of block 210 (resulting in more NO branch (exploit) decisions in block 210), as the learned treatment policy 113, π becomes more developed. The ε-greedy approach represents only one possible technique that could be used to make the block 210 decision. Any other suitable technique(s) could be used. Other non-limiting examples of techniques that could be used in block 210 include counter-based exploration and recency-based exploration. One non-limiting example of an additional or alternative technique for implementing the block 210 decision, together with the steps of block 215 or 220, is the so-called Boltzmann distributed exploration technique, wherein blocks 210, 215 and 220 are replaced with a selection of any action with probability related to the Boltzmann weight of the expected reward (from that action).

If the block 210 decision is positive, then method 200 proceeds to block 220, where an action a for the next time step is selected at random, after which method 200 proceeds to block 225. If the block 210 decision is negative, then method 200 proceeds to block 215, where an action a for the next time step is selected based on the treatment policy 113, π that has been learned so far in method 200—i.e. based on cumulative expected reward from the treatment policy 113, π that has been learned so far.

After selection of a next action a (in either block 215 or block 220), method 200 proceeds to block 225 which involves implementing the selected action a in a simulated environment. In practice, the next action a may involve specifying a set of radiation delivery parameters that represent delivering radiation with particular characteristics to a patient in the simulated environment of training method 200. The dose delivered to the simulated patient in the simulated environment may be estimated in block 225 according to known dose estimation techniques, which may include one or more models of the patient's body, one or more models of the patient geometry, including changes in patient geometry (e.g. patient movement and/or changes in the anatomical geometry of organs and/or target tissue).

Once the block 225 action has been implemented, method 200 proceeds to block 230 which involves determining the reward $r_t$ for the block 225 action just implemented. As discussed herein, the reward $r_t$ may comprise a metric which reflects how well the block 225 action performs in relation to achieving the treatment objectives 111A. It may be noted here that, in some implementations and/or circumstances, the reward $r_t$ may be not known at every state—or it might be known only in the end of treatment—or at the point when enough dose has been delivered to the target. In such circumstances, the block 230 determination may be made when it is possible to do so. Also, after implementing the block 225 action, method 200 performs the steps of block 235 which involve observing the treatment state s (including various observables about the simulated environment and the simulated patient) at the next time step (i.e. after implanting the block 225 action). By way of non-limiting example, such observables could include position information about the patient, radiation delivery parameters of the radiation delivery apparatus, estimated dose delivered to various voxels of the patient and/or the like. The block 235 treatment state may be based on training data 207. In currently preferred embodiments, any observation about the environment (including, without limitation, the patient) that may be utilized in the real treatment situation (e.g. method 100 of FIG. 4) may have a simulated counterpart in the simulation environment used during training (e.g. method 200 of FIG. 5).

Method 200 then proceeds to block 240 which involves collecting interaction data. The interaction data collected in block 240 may comprise: the block 205 treatment state (i.e. the treatment state prior to performing the block 225 action); the block 225 action; the block 230 reward; and the block 235 treatment state (i.e. the treatment state after performing the block 225 action). After collecting this interaction data in block 240, method 200 proceeds to block 245, where the block 240 interaction data is used to update the treatment policy 113, π. The treatment policy 113, π may be updated in block 245 in a direction that maximizes the cumulative expected reward. By way of non-limiting example, where method 200 implements a so-called Q-learning technique, the treatment policy 113, π involves selecting an action a that maximize expected reward $r_t$ and the actual learning is done by updating the expected reward $r_t$ for the selected action a at state s. That is, if in current state s, the action a actually leads to a larger (smaller) reward than expected, then the expected reward $r_t$ for action a in state s increases (decreases). To be more precise, it is not just the immediate reward, but also the observed new state s' (and expected reward associated with the new state s'). So, if action a in state s actually lead to a new state s' that has a high expected reward, then also the expected reward $r_t$ of action a in state s is increased. It should be noted that expected reward of state s may be understood as the maximum expected reward of any action in state s.

Method 200 then proceeds to inquiry 250. In block 250, if it is determined that the learning process should end (block 250 YES branch), then method 200 ends. Otherwise (block 250 NO branch) method 200 returns to block 205 for another iteration of blocks 205-250.

Returning now to FIG. 4, after the block 112 training, method 100 proceeds to radiation delivery process 114, which leverages the block 112 machine-learning based treatment policy 113, π to deliver radiation treatment to a subject S over a plurality of time steps. In the illustrated embodiment of FIG. 4, radiation delivery process 114 starts in optional block 120, which involves obtaining an initial treatment plan 123 for the fraction being delivered in method 100. Initial treatment plan 123 may be obtained as input to method 100 and may be ascertained using any suitable radiation delivery planning technique known in the art. An exemplary and non-limiting radiation delivery planning technique is described in Patent Cooperation Treaty application No. PCT/CA2006/001225, which is hereby incorporated herein by reference. In some embodiments, initial treatment plan 123 may be developed by treatment planning system 25C (FIG. 1) although this is not necessary. In some embodiments, an explicit initial treatment plan 123 is not necessary. For example, if an initial treatment state s of the subject was known and it is assumed that the subject being treated does not move at all, then application of the block 112 treatment policy 113, π would specify a treatment action a (e.g. a set of radiation delivery parameters) to be effected in each time step. Such a sequence of treatment actions may be understood to be an initial treatment plan 123, even although such an initial treatment plan may not be explicitly defined.

Initial treatment plan 123 may specify a series of actions a (radiation delivery parameters) over a series of time steps, which, when provided to radiation delivery apparatus 10, cause radiation delivery apparatus 10 to deliver an initially desired fractional dose to the patient over the series of time steps. However, initial treatment plan 123 may be understood to be fixed. Advantageously, radiation delivery process 114 of method 100 can accommodate unpredictable changes in the treatment state s of a patient (e.g. patient movement and/or the like) and controllably adjust radiation delivery actions a performed in each time step to accommodate such changes based on the treatment policy 113, π developed by machine learning (e.g. reinforcement learning) in block 112.

In the schematic illustration of FIG. 4, radiation delivery process 114 comprises an iterative loop between blocks 125 and 140. Each iteration of delivery process 114 and its constituent steps may involve AI agent 25 selecting and performing a particular action a (e.g. providing radiation delivery parameters to radiation delivery apparatus 10 to cause radiation delivery apparatus 10 to perform the action) for a corresponding time step (e.g. for a discrete time interval). The combination of block 114 iterations may provide a treatment fraction for a particular patient, wherein the treatment plan accommodates inter-fractional and/or intra-fractional changes in patient geometry based on the treatment policy 113, π learned in block 112.

In the illustrated embodiment of method 100, treatment delivery process 114 involves iteratively controlling a radiation delivery apparatus, such as exemplary apparatus 10, to deliver radiation to subject S in accordance with the block 112 treatment policy 113, π over a number of time steps. For any given time step, the decision on an action a to adopt for the next time step may be determined by AI agent 25 in block 130 based, at least in part, on evaluation of empirical observations at the current time step (and/or past time steps). Such empirical observations may include, for example, observations related to patient position and/or movement (e.g. patient geometry, as discussed above). The observations at the current time step (and/or past time steps) may be used by AI agent 25 in block 125 to determine a treatment state 127 for the current time step. Treatment state 127 at the current time step may thus comprise information about patient geometry. The decision on an action 133 to adopt for the next time step may be determined by AI agent 25 in block 130 based, at least in part, on evaluation of the block 125 treatment state 127 for the patient for the current time step. Given a treatment state 127 for the current time step, the block 112 treatment policy 113, π may map the current treatment state 127 to a particular action 133 (*a*). As discussed above, the output of AI agent 25 is an "action" 133 (*a*) which comprises manipulating or updating the radiation delivery parameters for the next time step. The updated radiation delivery parameters are then provided to radiation delivery apparatus 10 to cause radiation delivery apparatus 10 to deliver radiation to the patient in accordance with the radiation delivery parameters and in a manner which further fulfills a radiation treatment plan (e.g. approaches the block 110 radiation treatment objectives).

In some embodiments, AI agent 25 used in block 112 and in treatment delivery process 114 may be embodied by the same apparatus, such as is the case for AI agent 25 shown in treatment planning system 25C of the FIG. 1 embodiment. This is not necessary in general. In some embodiments, the AI agent that performs block 112 is separately embodied and trained on a separate suitable computing apparatus than the computing apparatus used to perform treatment delivery process 114. The block 112 treatment policy 113, π may be imported into the computing apparatus that performs treatment delivery process 114. The block 112 training process may generally be implemented on a different computing apparatus than that which performs treatment delivery process 114. The block 112 treatment policy 113, it may be embodied by any appropriate data structure storable in memory and executable by a data processor. Some non-limiting examples in which the treatment policy 113, it may be embodied include hash tables, vector arrays, tuples, and multi-dimensional tensors.

After optionally obtaining the initial treatment plan 123 in block 120, at any given time step, treatment delivery process 114 starts with block 125, where the AI Agent determines the current state of the treatment, or the "treatment state" 127 ($s_t$) for the current time step. The block 125 treatment state 127 ($s_t$) may generally comprise all information known to AI agent 25 up to the current time step. By way of non-limiting example, the information incorporated into treatment state 127 ($s_t$) may comprise: information in respect of observations made about the environment (including observations about the patient (e.g. patient geometry), about the radiation delivery apparatus 10 and/or the like) in the current time step and/or past time steps; information in respect of dose delivered to the patient (e.g. dose estimates) in the current time step and/or past time steps; and/or the like. Treatment state 127 ($s_t$) may, in some embodiments, be represented as a vector, array, or other similar data structure.

By way of specific and non-limiting examples, the information incorporated into treatment state 127 ($s_t$) may comprise any one or more of: accumulated treatment time (in the current fraction, in preceding fraction(s) and/or total treatment time); estimates of the dose delivered or characteristics of the dose delivered to various tissues (e.g. to target volume and OAR volumes) over the course of the current fraction and/or past fractions (e.g. 3D dose distribution reconstruction, mean dose, mean dose for particular volumes, fluence maps, dose-volume histograms, dose-at volume information, volume-at dose type aggregated dose information, geometrically equivalent dose, dose homogeneity indices and/or the like); indices and/or metrics related to temporal characteristics of the delivered dose in the current fraction and/or past fractions (e.g. indices related to how the fractionalization and/or dose delivery rate is impacting the biological impact of the delivered dose); observed or otherwise known characteristics of patient/tissue motion (e.g. direct measurements of patient motion; past measurements of patient respiratory activity); observed or otherwise known characteristics of radiation deliver apparatus 10 (e.g. MLC leaf speeds and positions, MLC jaws speeds and/or positions, gantry speed and/or position, couch speed and/or position).

Figure 6:
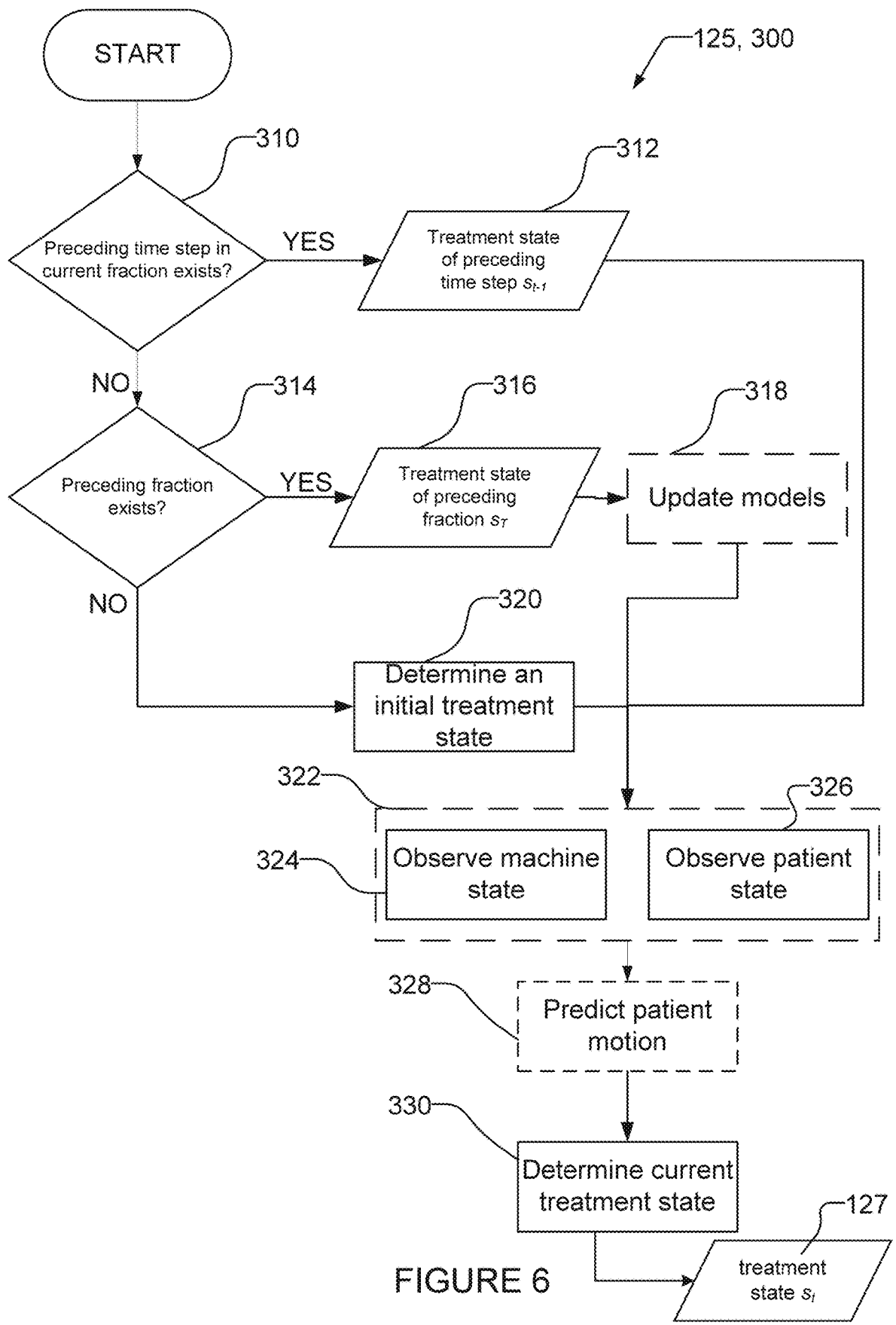
FIG. 6 is a flow chart illustrating a method of determining a current treatment state according to a particular embodiment of the invention.

FIG. 6 shows a non-limiting example embodiment of a method 300 that may be used for determining treatment state 127 ($s_t$) suitable for use in block 125 (FIG. 4). FIG. 6 starts in decision block 310, which evaluates whether there is a preceding time step in the current treatment fraction. If the block 310 evaluation is positive and there exists a preceding time step t−1, the treatment state observed/determined at the preceding time step $s_{t-1}$ (referred to herein as preceding treatment state 312) may be used as an input to method 300 for determining the current treatment state 127 ($s_t$) at the current time step t.

If the block 310 evaluation is negative, then method 300 proceeds to decision block 314 which evaluates whether a preceding treatment fraction exists. If the evaluation of decision block 314 is positive, the treatment state at the end of the preceding fraction at its final time step T is $s_T$ (referred to herein as preceding fraction end state 316) may be used as an input to method 300 for determining the current treatment state 127 ($s_t$). In block 318, preceding fraction end state 316 may be updated. The block 318 updates may include, by way of non-limiting example: modelling the passage of time between the end of the preceding fraction and the current fraction; updating patient images and/or other detected/sensed information about the patient including patient geometry; updating patient models (which may be based on updated patient images and/or other detected/sensed information about the patient including patient geometry); and/or the like. The block 318 updates may be based in part on sensed information, patient images, patient-specific models, population-based models and/or the like that are input to AI agent 25. The use of up to date sensed information, patient images and/or models in the block 318 updates may advantageously be used to account for inter-fraction variability in a patient's physiology (e.g. patient geometry) between treatment fractions—i.e. the machine-learning based treatment policy (applied in block 130 (FIG. 4)) may consider the most up-to-date information available about the patient's current state.

If the block 314 evaluation is negative, this represents the scenario where no preceding treatment fraction or time step exists (i.e. the beginning of a course of radiation treatment in accordance with a treatment plan—the first iteration of process 114 of method 100 (FIG. 4), where treatment state 127 is determined for the first time). In such cases, an initial treatment state $s_{t=0}$ may be determined in block 320. Such an initial treatment state $s_{t=0}$ may be an input to methods 100, 300. By way of non-limiting example, the block 320 initial treatment state may be based on one or more suitable patient images, other types of detected/sensed information about the patient including patient geometry, patient-specific models, population based models, known or determinable information in respect of radiation delivery apparatus 10, information input by a clinician and/or the like. In a non-limiting example embodiment, block 320 may involve AI agent 25 instantiating in memory a vector (or other suitable data structure) containing dose estimation variables with the values of the dose-estimation variables set to 0.

After defining an initial treatment state from the various possible past (or initial) treatment states (treatment state 312 ($s_{t-1}$) from a preceding time step, treatment state 316 ($s_T$) from a preceding fraction, and/or initial treatment state 320 ($s_{t=0}$), respectively), method 300 proceeds to process 322. Process 322 involves obtaining a set of environmental observations. Such environmental observations may include, by way of non-limiting example, observations 324 comprising information about the current state of radiation delivery apparatus 10, observations 326 comprising information about the current state of the patient (e.g. patient geometry) and/or the like. Such environmental observations can be based, without limitation, on suitable patient images, other types of detected/sensed information about the patient (including about the patient geometry), patient-specific models, population-based models, information input by a clinician and/or the like.

Block 324 may involve observing (e.g. sensing) information about radiation treatment delivery apparatus 10. The information determined in block 324 may be referred to herein as the machine state. By way of non-limiting example, the block 324 machine state information may comprise current measurements, operational parameters, and/or otherwise observable or known information about beam intensity of a radiation source, MLC leaf position, MLC orientation angle $\varphi$, gantry angle, couch position and/or the like. In some embodiments, some of the observables that make up the machine state are sensed by sensors external to the radiation delivery apparatus, such as through images or image streams captured from one or more cameras and/or other suitable sensors. In some embodiments, some of the observables that make up the machine state are sensed by sensors, systems and/or components that are part of radiation treatment system 10. In some embodiments, some such observables may be operational parameters or information otherwise known to control system 23 of radiation delivery apparatus 10 (FIG. 1). For example, the above-discussed radiation delivery parameters may be controlled by control system 23 of radiation delivery apparatus 10. In such circumstances, control system 23 is able to retrieve machine state parameters corresponding to such radiation delivery parameters (e.g. from an internal memory or otherwise) and supply them to AI agent 25 or any other software process performing block 324.

Block 326 involves observing (e.g. sensing) information about the current state of the patient. The information determined in block 326 may be referred to herein as the current patient state. By way of non-limiting example, the block 326 current patient state information may comprise observations about patient geometry. Non-limiting examples of how patient geometry observations may be obtained include making references from marker blocks and/or the relative positioning of the patient to fiducial markers. Patient geometry observations may also be obtained using captured images, such as images from body surface cameras, 2D kV x-ray images, 2D MV portal images, ultrasound images, magnetic resonance images and/or the like. In some embodiments, 3D images of the patient and the tissues of interest may be reconstructed from images obtained by any appropriate imaging modality. For example, in some embodiments 2D kV x-ray images could be used to reconstruct a 3D cone-beam CT image. Such 3D images may be automatically segmented during the performance of block 326 to delineate target volumes and OAR volumes.

The block 326 current patient state information may additionally or alternatively comprise observations about dose distribution to target volumes and OAR volumes. Such dose distribution may be measured and/or estimated using suitable patient-specific, population-based and/or empirical models. There are number of possible dosimetry instruments and methods that may be employed to quantitatively evaluate dose distribution to target tissues based on the characteristics of radiation that is delivered. As an illustrative example of dosimetry methods that may be employed at block 326, the COMPASS dose computation algorithm in conjunction with sensed ionization data from detector arrays may be used to calculate the dose distribution to a target volume within a patient during IMRT. Other possible techniques include positioning Exradin Model A1SL ionization chambers in appropriate locations proximate to volumes of interest to measure a delivered dose of radiation.

The exemplary dosimetry methods above describe point dose measurements which relate a single delivered dose of radiation to an absorbed dose in tissues. In some embodiments, block 326 observations produce cumulative dose distribution information. In some embodiments, 3DVH® software (and/or the like) may be used in conjunction with ArcCHECK® 3D diode array detectors (and/or the like) to produce dose-volume histograms (DVHs), which enable evaluating current treatment plan progress without the need for further processing.

In some embodiments, the block 326 patient state may additionally or alternatively be based on other types of detected/sensed information about the patient (including about the patient geometry), patient-specific models, population-based models, information input by a clinician and/or the like.

Figure 7:
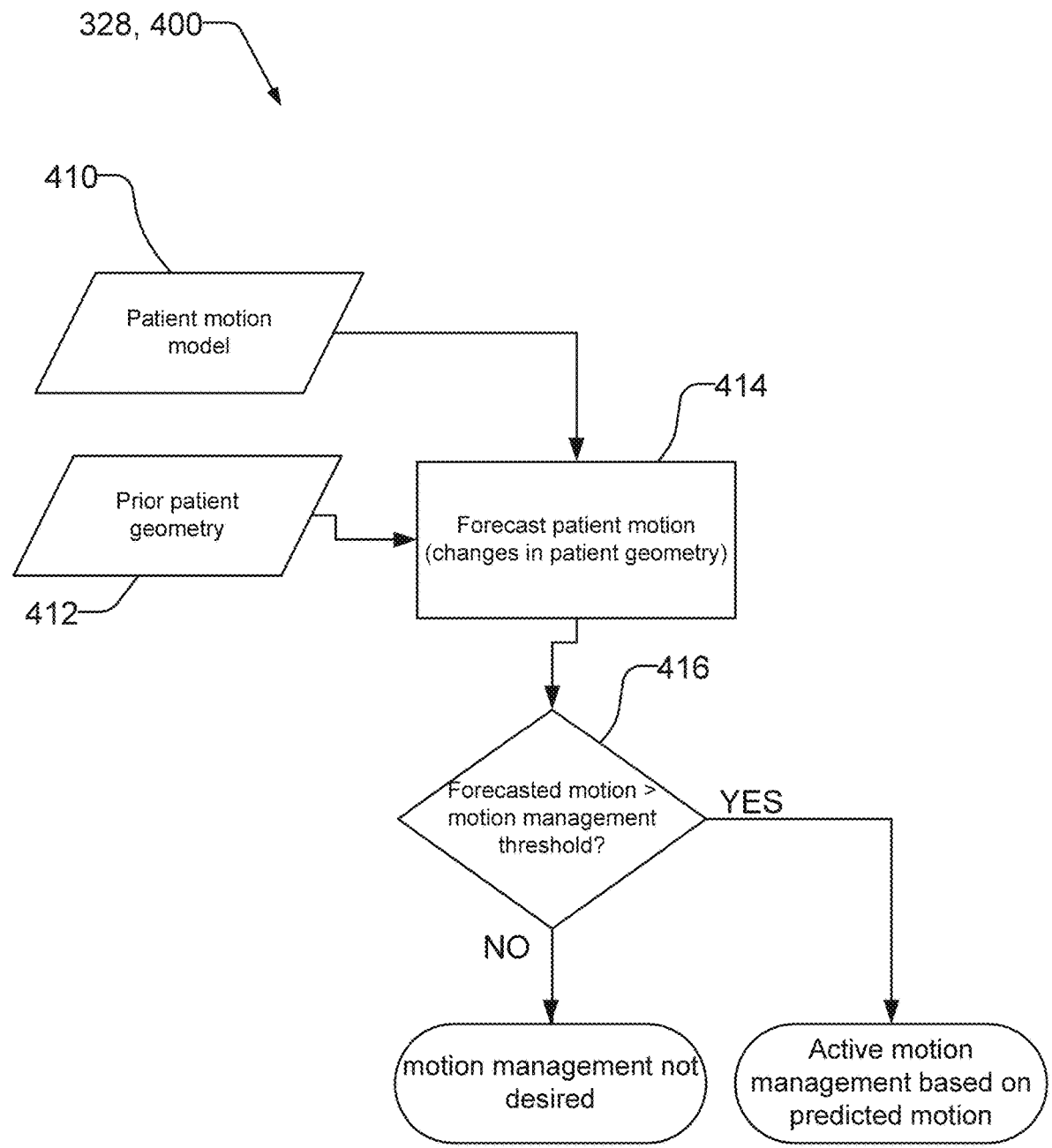
FIG. 7 is a flow chart illustrating a method for predicting patient motion according to a particular embodiment of the invention.

At the conclusion of process 322, after observations representing sensed information about the current machine state and the current patient state are obtained at blocks 324 and 326, respectively, method 300 may proceed to optional block 328 to predict expected patient motion (patient geometry). A non-limiting example of a method 400 for predicting patient geometry suitable for use in block 328 is shown in FIG. 7. Method 400 may estimate the expected displacement (e.g. updated geometry) of volumes of interest in the patient in the next time step, so that such expected patient displacement (geometry) information may be incorporated into the radiation delivery parameters for the next time step. In this way, delivery of radiation treatment in the next time step may accurately target the target volume(s) and avoid OAR volume(s). In the illustrated embodiment of method 400 (FIG. 7), a representative patient motion model 410 is supplied to method 400. Block 124 (FIG. 4) may be optionally performed as part of method 100 to produce patient motion model 410. It may be desirable for patient motion model 410 to capture expected variations in patient geometry in and around the volumes of interest in the radiation therapy treatment plan. For example, in the case of treating a tumor in a patient's brain, it may be desirable for patient motion model 410 to correlate the contribution of respiratory motion to the motion of the brain tumor and surrounding tissues in the patient's skull.

In an exemplary embodiment for performing block 124 (FIG. 4), a representative motion model for a patient based on respiratory action is obtained by analyzing multiple static 3D image sets obtained at consecutive time intervals. In another exemplary embodiment, 4D image sets are obtained and analyzed to arrive at the patient motion model. Such 4D image sets allow for reconstruction of multiple discrete 3D scans which can demonstrate the range of tissue motion and allow for path data of the tissues during intervening phases of respiration to be obtained. The analysis of image sets may comprise applying an image segmentation algorithm to identity the position and motion of volumes of interest between images and/or image frames. Any appropriate imaging modality may be used for obtaining image sets to be analyzed for determining the patient motion model. In some embodiments, computed tomography (CT), ultrasound imaging, magnetic resonance imaging modalities and/or the like are employed to acquire image sets capturing temporal variations in internal tissue positions. In some embodiments, observed motion of the patient's external surface may additionally or alternatively be used (and/or may be used as a surrogate) in conjunction with a model correlating the external motion to the motion of internal volumes. Other sources of expected voluntary and/or involuntary patient motion and their contributions to motion in volumes of interest may be modelled as well, either individually or in combination with each other, such as intestinal gas induced motion, gross patient movement (i.e. movement of a part of the patient's body) and/or the like. The various models which are produced may be combined in any appropriate manner such that the resultant block 124 patient motion model can accurately account for a variety of different expected patient motions during treatment.

In some embodiments, the patient motion model produced at block 124 may be specific to a patient undergoing radiation treatment (by way of treatment delivery process 114 in FIG. 4, for example). In such embodiments, image sets capturing the patient's motion may be obtained and analyzed to provide a basis for creating the patient motion model as described above prior to the delivery of radiation treatment by process 114. In some embodiments, determining the patient motion model at block 124 comprises employing a motion model of a reference patient and/or a reference population of patients. The reference patient motion model may be selected from a database containing motion models from various patient profiles (based on characteristics such as age, weight, sex, or height, for example), the database containing motion models which correlate patient movements to the movement in different tissues of interest. The patient profile conforming most closely to the present patient and a subset of the motion model pertaining to the volumes of interest may be selected from the database as the reference motion model. In some embodiments, the reference patient motion model is based at least in part on a population based statistical model—e.g. based on an average of a population of reference patients.

In some embodiments, the reference motion model may comprise 4D data which may be correlated to a static 3D image of a specific patient to perform block 124 and thereby produce the patient motion model 410. Such a correlation may be achieved using any appropriate numerical methods or algorithms, including techniques such as linear regression and machine learning. The use of a reference motion model as opposed to the bespoke modelling of each individual patient's motion could be preferable in scenarios where cost and/or time is/are a consideration, as the acquisition of 3D or 4D image sets can be a resource intensive process. Radiation dose delivered to the patient may also be minimized due to extensive CT or other imaging required in motion models based solely on imaging a particular patient. In an example embodiment, patient motion model 410 is represented by deformation and displacement matrices and/or tensors having key-value pairs representing the motion of one or more internal volumes at various points in a patient's respiratory cycle.

In conjunction with supplying patient motion model 410 as an input to method 400, prior patient geometry 412 may be supplied as an input to method 400. Prior patient geometry 412 may comprise information on the geometry of patient tissues and/or the patient him or herself in one or more preceding time steps. For example, prior patient geometry 412 may have a history length of l=3, comprising the geometry of patient tissues (and/or the patient) from 3 preceding time steps. In some embodiments, the patient geometry data $p_{t-3}$, $p_{t-2}$ and $p_{t-1}$ at each such time step may be represented as a matrix of the coordinates of discrete tissue/patient points (tissue/patient markers), for example. In some embodiments, the prior patient geometry $p_{t-3}$, $p_{t-2}$ and $p_{t-1}$ comprises spatial coordinates of a number of points on the tissues of interest within a patient at each of these preceding time steps. Prior patient geometry data $p_{t-3}$, $p_{t-2}$ and $p_{t-1}$ from preceding time steps may be embodied in prior patient geometry 412 and be contained in past treatment states $s_{t-1}$, $s_T$, and $s_{t=0}$ at blocks 312, 316, and 320 of method 300, for example. Furthermore, the determination of current patient geometry at the current time step $p_t$ may be obtained from observing the current patient state at block 326 of method 300.

At block 414 of method 400, the geometry of volumes of interest (e.g. target tissues, healthy tissues, OAR tissue and/or the patient generally) in a subsequent time step $\hat{p}_{t+1}$ may be estimated based on patient motion model 410 and/or prior patient geometry 412. In one example embodiment, patient motion (changes in patient geometry) may be predicted in block 414 by considering patient motion model 410 to describe a cyclic motion (such as the respiration cycle). Prior patient geometry 412 can be used to keep track of the current phase of the motion cycle, so the block 414 forecast may assume that the cycle will continue based on patient motion model 410. In some embodiments, multiple motion models 410 may be used to describe different possible time-dependent motions. Prior patient geometry 412 may then be used to find which motion model (if any) is correlated to the observed near history, and the block 414 forecast may comprise following the most highly correlated motion model.

After an estimate of patient motion (change in patient geometry) is obtained at block 414, method 400 proceeds to decision block 416 which evaluates whether the estimated patient motion (change in patient geometry) in the following time step exceeds a motion management threshold. The block 416 motion management threshold may represent a maximum acceptable displacement before intervention or modification of treatment parameters is desired (e.g. manual intervention, manual modification of the treatment, automatically stopping the treatment fraction and/od the like). In some embodiments, block 414 may determine an aggregated value representing the overall motion in voxels corresponding to tissues of interest, the aggregated value derived from the various voxels at which motion estimates are obtained.

As illustrative examples, the aggregated value may comprise an arithmetic sum of the estimated displacement at each voxel of interest or the aggregated value may comprise a weighted sum where weights are assigned to voxels based on some suitable metric. In some embodiments, a weight may be assigned to each voxel, based (at least in part) on the voxel's proximity to the center of a volume of interest (e.g. the volume of a target cancer or the volume of an OAR). In some embodiments, weights may be assigned to voxels representing motion of different tissues. For example, voxels representing motion of an OAR volume may be given a different weight than voxels representing motion of the target volume. In some embodiments, different weights may be assigned to different directions based on the orientation of the radiation source (radiation source 12, for example) with respect to the patient. For example, movement in directions more closely aligned with the direction defined by the unit vector of the beam's eye view (BEV) may be given lower weights, as patient motion in such directions may involve correspondingly low amounts of re-shaping of the aperture (e.g. defined by the shaping of MLC leaves 35) through which radiation is delivered. Conversely, movement in directions more closely aligned with directions transverse (e.g. orthogonal) to the BEV may be given higher weights as tissue motion in such directions may make it desirable for correspondingly greater adjustments of the aperture to deliver the same distribution of radiation. In some embodiments, the block 416 motion management threshold is 3 mm. In some embodiments, this threshold is 2 mm. In some embodiments, block 416 is not necessary. In some such embodiments, block 328 (FIG. 6) may assume that active motion management is not desired in any cases and that the machine-learned treatment policy 113, π is sufficient to address a complete range of the forecasted motion in the patient.

If the evaluation of decision block 416 is positive, this may be an indication that active motion management is desired in the current state and method 400 terminates. If the evaluation of decision block 416 is negative, then no active motion management is indicated in the current state and method 400 terminates.

Returning to method 300 (FIG. 6), the performance of block 328 through method 400 described above results in current observations regarding predicted patient motion and a determination on whether active motion management based on the predicted motion is desired. In some embodiments, there are multiple thresholds that are considered at decision block 416. For example, different active management measures may be taken based on the estimated patient motion exceeding increasing threshold values. In some embodiments, an estimated motion exceeding a maximum threshold indicates that the patient is moving outside of expected limits and that the automatic delivery of radiation treatment by the AI agent should be terminated (at least temporarily) until the patient's movement can be addressed.

In some embodiments, only observations about predicted patient motion are produced at block 328, without an assessment on whether active motion management is desired. In other words, the evaluation of decision block 416 of method 400 may be omitted and the output of block 328 (method 400) may comprise the forecasted target motion in block 414. In some such embodiments, consideration of whether active motion management should be prescribed may be deferred to block 130 of method 100 (FIG. 4), where the predicted patient motion may be incorporated into the expected reward of performing an action a based on the machine-learned treatment policy 113, it and the block 125 treatment state s. In some such embodiments, the treatment policy 113, it prescribes an action a which accounts for such estimated movement.

Block 328 is optional. In some embodiments, method 300 (block 125) does not involve predicted motion, but instead generates the current treatment state in block 330 based on machine state 324 and patient state 326 and patient motion is incorporated into treatment policy 113, it based on machine (e.g. reinforcement) learning.

Whether or not patient motion is predicted in optional block 328, method 300 (FIG. 6) proceeds to block 330, which comprises determining the current treatment state 127 ($s_t$) based on machine state 324, patient state 326 and, optionally, the block 328 predicted patient motion. The current treatment state 127 ($s_t$) also represents the current treatment state 127 ($s_t$) resulting from block 125 of method 100 (FIG. 4). Based on the observations and inputs of preceding steps in method 300, the treatment state 127 ($s_t$) determined at block 330 may comprise and/or be based on, without limitation, some or all of the following components:

Cumulative observations representing radiation treatment progress for a particular patient up to the current time step including:
accumulated treatment time, which may comprise the total elapsed time in the current treatment fraction, the total elapsed time in the current and previous treatment fractions, and the elapsed treatment time of each preceding treatment fraction;
cumulative delivered dose, which may comprise and/or be based on 3D dose distribution reconstruction (e.g. based on MLC, gantry and radiation source parameters and patient images which may define tissue types for various voxels), fluence maps of MLC and gantry configurations delivering radiation in prior time steps, dose-volume histograms, dose-at volume information, and volume-at dose type aggregated dose information; and/or a metric (e.g. a model-based metric) of a physiological impact of delivered radiation based on dose delivered in the current fraction and/or previous fractions.

Current observations of a current machine state comprising measurements or parameters about intensity of a radiation source, MLC leaf positions, MLC orientation, MLC jaw positions, gantry angle, couch position and orientation and/or the like.

Observations of a current patient state comprising measurements and/or sensor output about patient position and/or movement (patient geometry) and dose distribution information and/or physiological impact information about target volumes and OAR volumes.

Estimated patient motion (changes in patient geometry) in a subsequent time step and an indication of whether active motion management is desired or not.

In some example embodiments, various additional components of the treatment state may be updated at block 330 to reflect the current treatment state 127 ($s_t$) by performing some or all of the following steps:

1. updating the 3D CT image reconstructions of the volumes of interest;
2. updating 3D target volume and OAR volume delineations/segmentations;
3. transforming the prior cumulative delivered dose distribution to the current reconstructed 3D CT image by updating a dose matrix and/or physiological impact matrix; and
4. using the updated 3D CT image, current machine state measurements, and a dose calculation engine, calculating the addition of the dose delivered at the current time step to the dose matrix of step 3.

After the conclusion of method 300 (block 125 of method 100 in FIG. 4), method 100 proceeds to block 130 which involves the AI agent determining a next action 133 ($a$) using the policy 113, $\pi$ determined by machine learning in block 112. The action 133 ($a$) selected by the AI agent may comprise software instructions readable by a radiation delivery apparatus to manipulate or update a set of available radiation delivery parameters. The action 133 ($a$) selected by the AI agent may comprise the updated radiation delivery parameters themselves. By way of non-limiting example, the set of radiation delivery parameters may comprise a beam intensity of a radiation source (which includes the possibility of having an intensity value of 0 or OFF), a beam-on-time, an MLC leaf position, an MLC orientation, a gantry angle, a couch position and/or the like. A machine learning (e.g. reinforcement learning) treatment policy 113, $\pi$ is operable to recommend actions 133 ($a$) within the action space, the action space representing all of the manipulable radiation delivery parameters, such as the ones discussed herein, for a particular radiation delivery apparatus. As discussed previously herein, the action 133 ($a$) that is selected by the AI agent in block 130 may generally comprise the action 133 ($a$) that maximizes the cumulative reward of all future states.

If the current block 125 treatment state 127 ($s_t$) indicates that there is a requirement for active motion management, an appropriate action may be determined as part of block 130. There are a number of non-limiting possible scenarios with respect to the estimated patient motion. A first potential scenario comprises the estimated patient motion being less than a motion management threshold (such as a threshold used in decision block 416 (FIG. 7)). In this scenario, the current treatment state 127 ($s_t$) need not be altered and an appropriate action 133 ($a$) can be selected in block 125 based on the block 112 treatment policy 113, $\pi$ and the current treatment state 127 ($s_t$). A second potential scenario comprises the estimated patient motion being greater than a motion management threshold (such as a threshold used in decision block 416 (FIG. 7)). In this scenario, one or more components of the current treatment state 127 ($s_t$) may optionally be altered to reflect such movement. For example, new or updated transformations or image reconstructions may be applied to one or more planning images and/or reconstructed 3D CT images to reflect the estimated changes in patient geometry of volumes of interest. By doing so, the action 133 ($a$) determined at block 130 may appropriately account for expected changes to the treatment state 127 ($s_t$) stemming from large amounts of patient motion to arrive at a more optimized dose distribution delivery. As discussed above, the use of active motion management is optional. In some embodiments, the action 133 ($a$) selected in block 125 is determined based on the block 112 treatment policy 113, $\pi$ and the current treatment state 127 ($s_t$) without regard to active motion management.

In some embodiments, constraints which define "illegal" actions are known (e.g. by user input, by predefined operational parameters and/or the like) to treatment planning system 25C to represent undesirable parameter changes given a current state to limit the action space available to the AI agent from which it may select an action. Examples of possible constraints which define illegal actions at a given state include:

Radiation source 12 cannot travel further than a maximum distance between consecutive time steps. This may be achieved entirely, or in part, by imposing a maximum change in any motion axis between consecutive time steps. Separate constraints may be provided for each motion axis. For example, a maximum angular change may be specified for gantry angle, maximum changes in displacement may be provided for couch translation etc.

Parameters affecting beam shape cannot change by more than specified amounts between consecutive time steps. For example, maximum values may be specified for changes in the positions of leaves 36 of a MLC 35 or changes in the rotation orientation of MLC 35.

Parameters affecting beam shape cannot change by more than a specified amount per unit of motion axis change. For example, maximum values may be specified for changes in the positions of leaves 36 of a MLC 35 for each degree of rotation of gantry 16 about axis 18.

The source intensity cannot change by more than a specified amount between time steps.

The source intensity cannot change by more than a specified amount per unit of motion axis change.

The source intensity cannot exceed a certain level.

As discussed elsewhere herein, there constraints may be obtained in block 110 and may be incorporated into the optimization process as soft constraints (e.g. part of a reward function, objective function and/or the like) or hard constraints. Some or all of such constraints may be incorporated into the block 112 training (machine learning) process in addition to (or in the alternative to) incorporation into the block 130 action selection process.

The imposition of constraints may help to reduce total treatment time by accounting for the physical limitations of particular radiation delivery apparatus. For example, if a particular radiation delivery apparatus has a maximum radiation output rate and the AI agent selects an action comprising a radiation intensity that results in a radiation output rate higher than this maximum radiation output rate, then the rate of movement of the motion axes of the radiation delivery apparatus will have to slow down to deliver the prescribed intensity. Accordingly, a constraint imposed on the maximum source intensity can force a solution where the prescribed intensity is within the capability of the radiation delivery apparatus and the motion axes of the radiation delivery apparatus do not have to slow down. Since the motion axes do not have to slow down, such a solution can be delivered to subject S relatively quickly, causing a corresponding reduction in total treatment time. Those skilled in the art will appreciate that other constraints may be used to account for other limitations of particular radiation delivery apparatus and can be used to reduce total treatment time.

A non-limiting example of how such constraints may be defined is the following parameters should not change by more than the stated amounts between any two consecutive time steps:
  intensity—10%;
  MLC leaf position—5 mm;
  MLC orientation angle $\varphi$—5%;
  gantry angle—1 degree; and
  couch position—3 mm.

Once an appropriate action 133 (a) has been determined at block 130, process 114 proceeds to block 135, where the action 133 (a) is implemented by an appropriate treatment delivery apparatus, such as radiation delivery apparatus 10 (FIG. 1). As discussed elsewhere herein, an action 133 (a) may be implemented by an AI agent, such as AI agent 25 (FIG. 1), by providing a set of radiation delivery parameters to a radiation delivery apparats, to thereby cause the radiation delivery apparatus to implement the action defined by the radiation delivery parameters.

In some embodiments, a radiation delivery apparatus is configured such that its radiation source is moved intermittently between time steps. As an illustrative and non-limiting example, in embodiments where the radiation source is moved intermittently, the action 133 (a), selected in block 130 and implemented in block 135, may specify a gantry angle, an MLC leaf position, an MLC orientation angle, MLC jaw positions and/or the like. The radiation delivery apparatus is operated to move according to these parameters and upon finishing, the radiation source may be caused to deliver radiation at an intensity and for a beam-on-time as specified by the action 133. In some embodiments, other additional or alternative radiation delivery parameters may form part of action 133 (a).

In some embodiments, a radiation delivery apparatus is configured so that its radiation source is moved continuously along a trajectory. In such embodiments, the radiation intensity specified by the action 133 (a) is typically not delivered to the subject from a static gantry angle, but instead is delivered continuously throughout the portion of the trajectory 30 as the radiation source moves according to the current action 133 (a). The radiation output rate of the source 12 may be adjusted by the radiation delivery apparatus 10 and control system 23, so that the radiation dose to the target volume for that time step conforms to what is prescribed by the action 133 (a). In some embodiments, the radiation output rate of the radiation source may be one of the radiation delivery parameters provided by the AI agent to the radiation delivery apparatus as part of the action 133 (a) to be implemented. The radiation output rate will normally be determined by the amount of time required for the position of the radiation source 12 and the shape of the radiation beam to change between intervening time steps. In some embodiments, the treatment policy 113, $\pi$ may be constrained to chose actions 133 (a) having parameters which allow the motion of the radiation delivery apparatus to be continuous between adjacent time steps.

In some embodiments, the action 133 (a) determined at block 130 and implemented at block 135 accounts for latency inherent in any software operations that are performed by treatment planning system 25C and/or radiation delivery apparatus 10. Latency may be present, for example, when the AI agent performs state updates according to method 300, from latency in data acquisition from various sensors of radiation delivery apparatus 10, 3D image reconstructions, and dose distribution matrix updates. In some embodiments, such latency may be accounted for as a part of the block 112 training of AI agent 25.

Following the performance of the prescribed action 133 (a) at block 135, method 100 (FIG. 4) proceeds to decision block 140, which evaluates whether the block 110 treatment objectives have been met. If the evaluation at block 140 is positive and the treatment objectives have been met, then method 100 terminates. If the evaluation at block 140 is negative because the block 110 treatment objectives have not yet been met, method 100 performs another iteration of process 114 by determining the updated treatment state at block 125 in the subsequent time step. In some embodiments, decision block 140 evaluates whether the treatment objectives of a current treatment fraction have been met to a within a clinically acceptable tolerance. In such embodiments, the treatment state 125 of the immediately preceding iteration represents the terminal state of the current treatment fraction and may be used as an initial state (for example in treatment state 316 (FIG. 6)) in a subsequent treatment fraction.

A person skilled in the art may select from a number of possible training (machine-learning) algorithms for training an AI agent to develop a treatment policy 113, $\pi$ at block 112 of method 100. Some forms of learning may have particular application and relevance to the task of training an AI agent in the field of radiation therapy, more specifically, in the field of IMRT. For example, transfer learning is a machine learning method where findings gained in learning to perform one task can help speed up training and improve learning in a related but different task. In some embodiments, transfer learning may be employed at block 112 to provide a pre-existing AI agent and treatment policy to serve as a starting point for training an AI agent to a specific patient. In such embodiments, it is preferable to use a pre-existing model having a close correspondence in treatment factors such as target volume, OAR volumes, and desired dose distribution, for example. In other embodiments, a general AI agent may be trained against a large population of patients undergoing similar radiation treatments. Such agents may be used for delivering radiation therapy to patients without the need for any patient specific training and may only involve optional patient specific validation.

Common to many of the training algorithms discussed herein is the provision of a simulated treatment environment. The simulated treatment environment comprises digital representations of the radiation delivery apparatus and a patient (which can either be a generalized patient or a specific patient). In some embodiments, the digital representation of the radiation delivery apparatus is simply a validator that checks that a requested machine state is possible from kinematic equations modelling various components of the treatment apparatus (e.g. gantry 16, couch 15, MLC 35 and/or the like). In such embodiments, simulated observations of the machine state (such as in block 324 of method 300) may comprise current axis values of the various treatment apparatus components. In some embodiments, the simulated treatment apparatus represents an idealized model of the apparatus used during treatment. In other embodiments, real world inaccuracies inherent in machines may be incorporated in the simulated treatment apparatus, for example, expected inaccuracies from backlash or from finite acceleration constraints.

The simulated treatment apparatus may additionally comprise a simulated radiation source to deliver doses of radiation to the simulated patient. Various software packages and algorithms are known in the art for simulating medical linear accelerators. For example, EGSnrc, BEAM, and GEANT4 are all exemplary software toolkits used to perform Monte Carlo simulations of ionizing radiation transport through matter. For simulating the aperture defined by leaves of an MLC, software libraries and toolkits are available to further compute phase-space data of radiation beams passing through and MLC aperture, such as that provided by the PRIMO project.

The digital representation of the patient can be accomplished in a number of possible ways. In some embodiments, a set of 3D CT images and a patient motion model (such as that obtained in block 124) may form the digital representation of the patient. In other embodiments, the digital representation of the patient may comprise a 4D CT image set to represent temporal changes in patient motion. Simulated observations of the patient state (such as in block 324 of method 300) may comprise imposing patient movement from a patient motion model to 3D CT images through any appropriate technique, such as deformable reconstruction. Other sensor readings embodied in patient state observations may be obtained through simulation sensor readings and/or appropriate processing. Exemplary examples of this include reconstructed projection delineating target volumes or simulated locations of marker blocks. Many other simulated observations appropriate to the specific simulation treatment scenario are possible and should be apparent to those skilled in the art. Simulation of the absorbed dose during the simulated treatment can be performed using any appropriate software tools. For example, the EGSnrc toolkit mentioned above contains functionality to calculate a quantity of absorbed dose.

INTERPRETATION OF TERMS

Unless the context clearly requires otherwise, throughout the description and the
- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Software and other modules may reside on servers, workstations, personal computers, tablet computers, image data encoders, image data decoders, PDAs, color-grading tools, video projectors, audio-visual receivers, displays (such as televisions), digital cinema projectors, media players, and other devices suitable for the purposes described herein. Those skilled in the relevant art will appreciate that aspects of the system can be practised with other communications, data processing, or computer system configurations, including: Internet appliances, hand-held devices (including personal digital assistants (PDAs)), wearable computers, all manner of cellular or mobile phones, multi-processor systems, microprocessor-based or programmable consumer electronics (e.g., video projectors, audio-visual receivers, displays, such as televisions, and the like), set-top boxes, color-grading tools, network PCs, mini-computers, mainframe computers, and the like.

The invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Where a record, field, entry, and/or other element of a database is referred to above, unless otherwise indicated, such reference should be interpreted as including a plurality of records, fields, entries, and/or other elements, as appropriate. Such reference should also be interpreted as including a portion of one or more records, fields, entries, and/or other elements, as appropriate. For example, a plurality of "physical" records in a database (i.e. records encoded in the database's structure) may be regarded as one "logical" record for the purpose of the description above and the claims below, even if the plurality of physical records includes information which is excluded from the logical record.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments". Such features are not mandatory and may not be present in all embodiments. Embodiments of the invention may include zero, any one or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

The invention claimed is:

1. A method for determining a radiation dose to deliver to a patient using a radiation delivery apparatus, the method comprising:
  providing a radiation delivery apparatus comprising a radiation source and one or more moveable elements;
  defining a machine state, the machine state comprising positions of the one or more moveable elements and wherein, when the radiation source is active, the machine state defines characteristics of radiation emitted by the radiation delivery apparatus;
  for each of a plurality of time steps in a radiation delivery fraction:
  receiving, at an artificial intelligence (AI) agent comprising a processor configured to execute software instructions: a set of observations regarding the machine state and regarding geometry of the patient;
  determining, by the AI agent, a current treatment state of the patient based at least in part on the set of observations;
  determining, by the AI agent, a next action comprising a next machine state for a subsequent time step based at least in part on the current treatment state and an artificial intelligence (AI) policy determined a priori using a machine-learning process executed on training data, the next machine state for the subsequent time step defining characteristics of radiation to be emitted by the radiation delivery apparatus in the subsequent time step,
  wherein determining, by the AI agent, the current treatment state of the patient comprises:
    determining whether there is a preceding time step in the radiation delivery fraction; and determining whether the patient has been subjected to radiation treatment in a previous radiation delivery fraction, wherein the current treatment state of the patient is determined:
- based at least in part on a preceding treatment state of the patient determined as part of the preceding time step when there is a preceding time step in the radiation delivery fraction;
- based at least in part on a preceding treatment state determined at a conclusion of the previous radiation delivery fraction when there is no preceding time step in the radiation delivery fraction and the patient has been subjected to radiation treatment in the previous radiation delivery fraction; and
- based at least in part on defining an initial treatment state when there is no preceding time step in the radiation delivery fraction and the patient has not been subjected to radiation treatment in the previous radiation delivery fraction.

2. A method according to claim 1 wherein the one or more moveable elements comprise one or more of: a plurality of aperture-defining elements whose positions, in combination, define an aperture through which radiation from the radiation source is directable; a radiation source-moving element whose position defines an orientation at which radiation from the radiation source is directable.

3. A method according to claim 1 wherein when it is determined that there is no preceding time step in the radiation delivery fraction and that the patient has been subjected to radiation treatment in the previous radiation delivery fraction the method comprises determining, by the AI agent, the current treatment state of the patient based at least in part on patient geometry determined using image data taken from the patient after the previous radiation delivery fraction.

4. A method according to claim 1 wherein the current treatment state of the patient comprises estimated geometries of voxels of interest within the patients body, the estimated geometries being based at least in part on observations regarding a geometry of the patient.

5. A method according to claim 4 comprising determining, by the AI agent, the estimated geometries based at least in part on the observations regarding the geometry of the patient and one or more models of patient movement.

6. A method according to claim 5 wherein the one or more models of patient movement comprise a model of changes in patient geometry due to respiration.

7. A method according to claim 5 wherein the one or more models of patient movement comprise models which predict changes in geometry of voxels in an interior of the patients body based on a change in geometry of an exterior of the patient's body.

8. A method according to claim 5 wherein the one or more models of patient movement are based at least in part on a plurality of images of the patient obtained over a period of time prior to the radiation delivery fraction.

9. A method according to claim 1 wherein determining the current treatment state of the patient comprises determining an estimated cumulative dose absorbed by target tissue during the radiation delivery fraction.

10. A method according to claim 9 wherein determining the current treatment state of the patient comprises:
- updating a 3D image reconstruction of volumes of interest within the patients body based on observations regarding a geometry of the patient;
- transforming a cumulative dose absorbed by the target tissue in a preceding time step to the updated 3D image reconstruction; and
- estimating an additional dose delivered to the target tissue at a current time step based at least on the updated 3D image reconstruction, observations regarding the machine state at the current time step, and a dose estimation engine;
- wherein determining the estimated cumulative dose absorbed by the target tissue during the radiation delivery fraction comprises determining a sum of a transformed cumulative dose from the preceding time step and the additional dose.

11. A method according to claim 9 wherein determining the current treatment state of the patient comprises determining an accumulated treatment time during the radiation delivery fraction.

12. A method according to claim 1 wherein determining the current treatment state of the patient comprises determining an estimated cumulative dose absorbed by a non-target organ of the patient during the radiation delivery fraction.

13. A method according to claim 1 wherein the AI policy comprises a mapping and wherein determining, by the AI agent, the next action comprising the next machine state for the subsequent time step comprises creating a correspondence from the current treatment state to the next action using the mapping.

14. A method according to claim 13 wherein the mapping, in creating the correspondence from the current treatment state to the next action, is based on maximizing a reward function which maximizes a cumulative reward obtained over all expected subsequent time steps.

15. A method according to claim 1 comprising imposing on the AI agent, at each of the plurality of time steps in the radiation delivery fraction, a set of one or more constraints, the set of one or more constraints limiting a space of options available to the AI agent for determining the next action.

16. A method according to claim 15 wherein the set of one or more constraints comprise one or more of:
- a maximum distance that the radiation source may travel between a current time step and the subsequent time step;
- maximum distances that the one or more moveable elements may travel between the current time step and the subsequent time step;
- a maximum change in the intensity of the radiation source between the current time step and the subsequent time step; and
- a maximum value in the intensity of the radiation source.

17. A method according to claim 1 comprising training the AI agent to determine the AI policy using a reinforcement based machine-learning process together with the training data.

18. A method for delivering a radiation dose to a patient using a radiation delivery apparatus, the method comprising:
- providing a radiation delivery apparatus comprising a radiation source and one or more moveable elements;
- defining a machine state, the machine state comprising positions of the one or more moveable elements and wherein, when the radiation source is active, the machine state defines characteristics of radiation emitted by the radiation delivery apparatus;
- for each of a plurality of time steps in a radiation delivery fraction:
- receiving, at an artificial intelligence (AI) agent comprising a processor configured to execute software instructions: a set of observations regarding the machine state and regarding geometry of the patient;

determining, by the AI agent, a current treatment state of the patient based at least in part on the set of observations;

determining, by the AI agent, a next action comprising a next machine state for a subsequent time step based at least in part on the current treatment state and an artificial intelligence (AI) policy determined a priori using a machine-learning process executed on training data, the next machine state for the subsequent time step defining characteristics of radiation to be emitted by the radiation delivery apparatus in the subsequent time step; and causing the apparatus to perform the next action to thereby achieve the next machine state in the subsequent time step, wherein determining, by the AI agent, the current treatment state of the patient comprises:
  determining whether there is a preceding time step in the radiation delivery fraction; and
  determining whether the patient has been subjected to radiation treatment in a previous radiation delivery fraction, wherein the current treatment state of the patient is determined:
  based at least in part on a preceding treatment state of the patient determined as part of the preceding time step when there is a preceding time step in the radiation delivery fraction;
  based at least in part on a Preceding treatment state determined at a conclusion of the previous radiation delivery fraction when there is no preceding time step in the radiation delivery fraction and the patient has been subjected to radiation treatment in the previous radiation delivery fraction; and
  based at least in part on defining an initial treatment state when there is no preceding time step in the radiation delivery fraction and the patient has not been subjected to radiation treatment in the previous radiation delivery fraction.

19. A system for delivering a radiation dose to a patient, the system comprising:
  a radiation source; and
  one or more moveable elements;
  an artificial intelligence (AI) agent, the AI agent configured to:
    define a machine state, the machine state comprising positions of the one or more moveable elements and wherein, when the radiation source is active, the machine state defines characteristics of radiation emitted by a radiation delivery apparatus; and
  for each of a plurality of time steps in a radiation delivery fraction:
    receive a set of observations regarding the machine state and regarding geometry of the patient;
    determine a current treatment state of the patient based at least in part on the set of observations;
    determine a next action comprising a next machine state for a subsequent time step based at least in part on the current treatment state and an artificial intelligence (AI) policy determined a priori using a machine-learning process executed on training data, the next machine state for the subsequent time step defining characteristics of radiation to be emitted by the radiation delivery apparatus in the subsequent time step; and
    cause the radiation delivery apparatus to perform the next action to thereby achieve the next machine state in the subsequent time step,
  wherein determining the current treatment state of the patient comprises:
    determining whether there is a preceding time step in the radiation delivery fraction; and
    determining whether the patient has been subjected to radiation treatment in a previous radiation delivery fraction,
  wherein the current treatment state of the patient is determined,
    based at least in part on a preceding treatment state of the patient determined as part of the preceding time step when there is a preceding time step in the radiation delivery fraction;
    based at least in part on a preceding treatment state determined at a conclusion of the previous radiation delivery fraction when there is no preceding time step in the radiation delivery fraction and the patient has been subjected to radiation treatment in the previous radiation delivery fraction; and
    based at least in part on defining an initial treatment state when there is no Preceding time step in the radiation delivery fraction and the patient has not been subjected to radiation treatment in the previous radiation delivery fraction.

* * * * *